(12) United States Patent
Mergelsberg et al.

(10) Patent No.: US 10,000,493 B2
(45) Date of Patent: *Jun. 19, 2018

(54) PROCESS AND INTERMEDIATES FOR THE SYNTHESIS OF 8-[{1-(3,5-BIS-(TRIFLUORO-METHYL)PHENYL)-ETHOXY}-METHYL]-8-PHENYL-1,7-DIAZA-SPIRO[4.5]DECAN-2-ONE COMPOUNDS

(71) Applicant: OPKO HEALTH, INC., Miami, FL (US)

(72) Inventors: Ingrid Mergelsberg, Mahwah, NJ (US); Dominik Hermann Scherer, Horw (CH); Monika Erika Huttenloch, Kriens (CH); Hon-Chung Tsui, East Brunswick, NJ (US); Sunil Paliwal, Monroe Township, NJ (US); Neng-Yang Shih, Lexington, MA (US)

(73) Assignee: OPKO Health, Inc., Miami, FL (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/043,129

(22) Filed: Feb. 12, 2016

(65) Prior Publication Data

US 2017/0008893 A1 Jan. 12, 2017

Related U.S. Application Data

(60) Continuation of application No. 14/039,367, filed on Sep. 27, 2013, now Pat. No. 9,260,428, which is a division of application No. 12/531,859, filed as application No. PCT/US2008/003640 on Mar. 20, 2008, now Pat. No. 8,552,191.

(60) Provisional application No. 60/919,666, filed on Mar. 22, 2007.

(51) Int. Cl.
| | | |
|---|---|---|
| *C07D 471/10* | (2006.01) | |
| *C07D 211/38* | (2006.01) | |
| *C07D 498/10* | (2006.01) | |
| *C07D 211/56* | (2006.01) | |

(52) U.S. Cl.
CPC .......... *C07D 471/10* (2013.01); *C07D 211/38* (2013.01); *C07D 211/56* (2013.01); *C07D 498/10* (2013.01)

(58) Field of Classification Search
None
See application file for complete search history.

(56) References Cited

U.S. PATENT DOCUMENTS

| | | | |
|---|---|---|---|
| 3,094,522 A | 6/1963 | Patchett et al. | |
| 5,620,989 A | 4/1997 | Harrison et al. | |
| 5,760,018 A | 6/1998 | Baker et al. | |
| 6,162,805 A | 12/2000 | Hefti | |
| 6,215,019 B1 | 4/2001 | Pederson et al. | |
| 6,436,928 B1 | 8/2002 | Shih et al. | |
| 6,635,639 B2 | 10/2003 | Arora et al. | |
| 7,041,682 B2 | 5/2006 | Shih et al. | |
| 7,049,320 B2 | 5/2006 | Paliwal et al. | |
| 7,122,677 B2 | 10/2006 | Reichard et al. | |
| 7,354,922 B2 | 4/2008 | Xiao et al. | |
| 7,563,801 B2 | 7/2009 | Qiu et al. | |
| 7,709,641 B2 | 5/2010 | Shah et al. | |
| 7,902,366 B2 | 3/2011 | Paliwal et al. | |
| 7,981,905 B2 | 7/2011 | Qiu et al. | |
| 8,026,364 B2 | 9/2011 | Shah et al. | |
| 8,178,550 B2 | 5/2012 | Hu et al. | |
| 8,273,895 B2 | 9/2012 | Paliwal et al. | |
| 8,361,500 B2 | 1/2013 | Qiu et al. | |
| 8,404,702 B2 | 3/2013 | Qiu et al. | |
| 8,470,842 B2 | 6/2013 | Hu et al. | |
| 8,552,191 B2 | 10/2013 | Mergelsberg et al. | |
| 8,754,216 B2 | 6/2014 | Shah et al. | |
| 8,796,299 B2 | 8/2014 | Paliwal et al. | |
| 9,260,428 B2 | 2/2016 | Mergelsberg et al. | |
| 9,345,692 B2 | 5/2016 | Qiu et al. | |
| 9,469,629 B2 | 10/2016 | Palani et al. | |
| 2001/0029297 A1 | 10/2001 | Ashwood et al. | |
| 2003/0158173 A1 | 8/2003 | Paliwal et al. | |
| 2006/0007540 A1 | 1/2006 | Okuyama | |
| 2006/0094720 A1 | 5/2006 | Shih et al. | |
| 2006/0223804 A1 | 10/2006 | Shah et al. | |
| 2007/0244142 A1 | 10/2007 | Hu et al. | |
| 2008/0003640 A1 | 1/2008 | Hsu et al. | |
| 2010/0048601 A1 | 2/2010 | Hu et al. | |
| 2010/0087426 A1 | 4/2010 | Mergelsberg et al. | |
| 2010/0104637 A1 | 4/2010 | Qiu et al. | |
| 2010/0190759 A1 | 7/2010 | Palani et al. | |
| 2011/0038925 A1 | 2/2011 | Wan et al. | |
| 2011/0098468 A1 | 4/2011 | Paliwal et al. | |
| 2012/0295879 A1 | 11/2012 | Palani et al. | |
| 2013/0122088 A1 | 5/2013 | Qiu et al. | |
| 2013/0281477 A1 | 10/2013 | Hu et al. | |
| 2014/0031549 A1 | 1/2014 | Wu et al. | |
| 2014/0336158 A1 | 11/2014 | Paliwal et al. | |

FOREIGN PATENT DOCUMENTS

| | | |
|---|---|---|
| CN | 1606545 A | 4/2005 |
| EP | 0790248 A1 | 8/1997 |
| EP | 0850902 A1 | 7/1998 |
| EP | 3138836 A1 | 3/2017 |
| WO | WO-94/10165 A1 | 5/1994 |
| WO | WO-94/13639 A1 | 6/1994 |
| WO | WO-95/19344 A1 | 7/1995 |
| WO | WO-99/51344 A1 | 10/1999 |
| WO | WO-00/71554 A2 | 11/2000 |
| WO | WO-01/44200 A2 | 6/2001 |

(Continued)

OTHER PUBLICATIONS

U.S. Appl. No. 13/062,454, Wu et al.
U.S. Appl. No. 13/734,432, Qiu et al.

(Continued)

*Primary Examiner* — Samantha L Shterengarts
(74) *Attorney, Agent, or Firm* — Choate, Hall & Stewart LLP; Kristen C. Buteau; Michael A. Shinall

(57) ABSTRACT

This application discloses a process to synthesize 8-({1-(3,5-Bis-(trifluoromethyl)phenyl)-ethoxy)-methyl]-8-pheny-1,7-diazaspiro[4.5]decan-2-one comprising reacting a compound of the Formula 27a-sulfonate with zinc in the presence of acetic acid.

1 Claim, No Drawings

(56) References Cited

FOREIGN PATENT DOCUMENTS

| | | |
|---|---|---|
| WO | WO-02/14376 A2 | 2/2002 |
| WO | WO-03/051840 A1 | 6/2003 |
| WO | WO-2004/035596 A1 | 4/2004 |
| WO | WO-2005/100358 A1 | 10/2005 |
| WO | WO-2006/007540 A2 | 1/2006 |
| WO | WO-2006/065654 A1 | 6/2006 |
| WO | WO-2007/003135 A1 | 1/2007 |
| WO | WO-2007/114921 A2 | 10/2007 |
| WO | WO-2007/114922 A2 | 10/2007 |
| WO | WO-2007/117486 A2 | 10/2007 |
| WO | WO-2008/118328 A2 | 10/2008 |
| WO | WO-2008/118331 A2 | 10/2008 |
| WO | WO-10/028232 A1 | 3/2010 |
| WO | WO-2011/019911 A1 | 2/2011 |

OTHER PUBLICATIONS

U.S. Appl. No. 13/847,242, Qui et al.
U.S. Appl. No. 14/540,635, Qiu et al.
Cogan, D. et al., Asymmetric Synthesis of Chiral Amines by Highly Diastereoselective 1,2-Additions of Organometallic Reagents to N-tert-Butanesulfinyl Imines, Tetrahedron, 55:8883-8904 (1999).
Database Registry Chemical Abstracts Service, Columbus, Ohio, Accession No. RN 1065272-03-8, Entered STN:Oct. 23, 2008.
Duffy, R.A., Potential therapeutic targets for neurokinin-1 receptor antagonists, Expert Opinion on Emerging Drugs, 9(1):9-21 (2004).
English translation of Knabe, J. et al., Racemates and Enantiomers of Basic Substituted 5-Phenylhydantoins, Pharmazie, 52(12):912-919 (1997).
English translation of Schulte, K.E. et al., Hydantoin-Derivate as Potential Anti-inflammatory Substances, European Journal of Medical Chemistry-Chimica Therapeutica, 13(1 ):25-31 (1978).
Giard, T. et al., Pyrrolidines bearing a quaternary α-stereogenic center. Part 1: Synthesis of analogs of ABT-418, a powerful nicotinic agonist, Tetrahedron Letters, 40:5495-5497 (1999).
Gonzales, J.A. et al., Antiemetic Agents in Cancer Chemotherapy, Oncology Special Edition, 5:53-58 (2002).
Harrison, T. et al., Gem-Disubstituted Amino-Ether Based Substance P Antagonists, Bioorganic & Medicinal Chemistry Letters, 4(23):2733-2734 (1994).
Hill, R.K. Synthesis of spirolactams from nitrocycloalkanes, Journal of Organic Chemistry, 22:830-2 (1957).
Ikeda, M. et al., Synthetic studies on cephalotaxus alkaloids, a synthesis of (±)-cephalotaxine, Chemical and Pharmaceutical Bulletin, 41(2):276-81 (1993).

International Search Report for PCT/US02/40203, 4 pages (dated Apr. 24, 2003).
International Search Report for PCT/US08/003640, 6 pages (dated Jan. 20, 2009).
International Search Report for PCT/US2009/056020 (WO 2010/028232) dated Jan. 4, 2010.
Knabe, J. et al., Racemates and Enantiomers of Basic Substituted 5-Phenylhydantoins, Pharmazie, 52(12):912-919 (1997).
Kocienski, P.J. et al., Amino Protecting Groups, Thieme, pp. 512-516 (2005).
Kramer, M. et al., Distinct Mechanism for Antidepressant Activity by Blockade of Central Substance P Receptors, Science, 281:1640-1645 (1998).
Kubik, S. et al., Synthesis of α, α-Dialkylated Amino Acids with Adenine of Thymine Residues a New Mild and Facile Hydrolysis of Hydantoins, Tetrahedron Letters, 35(36):6635-6638 (1994).
Kurti, L. et al., Strategic applications of named reactions in organic synthesis: Background and detailed mechanisms, Science, pp. 286-287 (2005).
O'Donnell, M.J. et al., New Methodology for the Synthesis of α,α-Dialkylamino Acids Using the 'Self-Regeneration of Stereocenters' Method: α-Ethyl-α-Phenylglycine, Heterocycles, 46:617-630 (1997).
Oh, C. H. et al., Synthesis of New Hydantoin-3-Acetic Acid Derivatives , Bulletin of the Korean Chemical Society, 9(4):231-235 (1988).
Rogiers, J. et al., Stereoselective Conversion of 2H-1,4-oxazin-2-ones into 2,5,5-substituted piperidine-2-carboxamides and 2-methanamines and related octahydro-2H-pyrido[1 ,2-a]pyrazines, potential substance P antagonists, Tetrahedron, 57:8971-8981 (2001).
Rombouts, F.J.R. et al., Intramolecular Diels-Alder reactions of N-alkenyl-2(1 H)-pyrazinones: generation of a novel type of cis-1, 7-naphthyridine, Tetrahedron Letters, 42:7397-7399 (2001).
Schulte, K.E. et al., Hydantoin-Derivate as Potential Anti-inflammatory Substances, European Journal of Medical Chemistry—Chimica Therapeutica, 13(1 ):25-31 (1978).
Wallace, Exploiting catalyst characteristics: A protocol for increasing diastereoselectivity in a double ring-closing metathesis reaction, Journal of Molecular Catalysis A: Chemical, 254: 78-84, (2006).
Written Opinion, PCT/US2008/003640, dated Sep. 22, 2009, 11pages.
Wu, X et al., Stereoselective Transformation of 2H-1,4-Oxazin-2-ones into 2, (2), 5, 5-Tri- and Tetrasubstituted Analogues of cis-5-Hydroxy-2-piperidinemethanol and cis-5-Hydroxy-6-oxo-2-piperidinecarboxylic Acid, Tetrahedron, (56):3043-3051 (2000).
Wu, X. et al., Generation of Cyclopenta[c]piperidines and Pyrrolo[3,4-c]piperidines-Potential Substance P Antagonists-from Adducts of Cyclic Dienophiles and 5-Chloro-6-methyl-3-phenyl-2H-1 ,4-oxazin-2-one, Tetrahedron, 56:6279-6290 (2000).

PROCESS AND INTERMEDIATES FOR THE SYNTHESIS OF 8-[{1-(3,5-BIS-(TRIFLUORO-METHYL)PHENYL)-ETHOXY}-METHYL]-8-PHENYL-1,7-DIAZA-SPIRO[4.5]DECAN-2-ONE COMPOUNDS

CROSS REFERENCE TO RELATED APPLICATIONS

This application is based on and claims the priority of U.S. Provisional Application No. 60/919,666, filed Mar. 22, 2007, which is incorporated herein by reference in its entirety.

FIELD OF THE INVENTION

This application discloses a novel process for the preparation of 8-[{1-(3,5-Bis-(trifluoromethyl)phenyl)-ethoxy}-methyl]-8-phenyl-1,7-diaza-spiro[4.5]decan-2-one compounds, which have utility, for example, as NK-1 receptor antagonist compounds, and intermediates useful in the synthesis thereof.

BACKGROUND OF THE INVENTION

Identification of any publication, patent, or patent application in this section or any section of this application is not an admission that such publication is prior art to the present invention.

The preparation of diazaspirodecan-2-ones for example, 8-[{1-(3,5-Bis-(trifluoromethyl)phenyl)-ethoxy}-methyl]-8-phenyl-1,7-diaza-spiro[4.5]decan-2-one, for example, (5S,8S)-8-[{(1R)-1-(3,5-Bis-(trifluoromethyl)phenyl)-ethoxy}-methyl]-8-phenyl-1,7-diazaspiro[4.5]decan-2-one (the compound of Formula I) has been described in U.S. Pat. No. 7,049,320 (the '320 patent), issued May 23, 2006, the disclosure of which is incorporated herein in its entirety by reference.

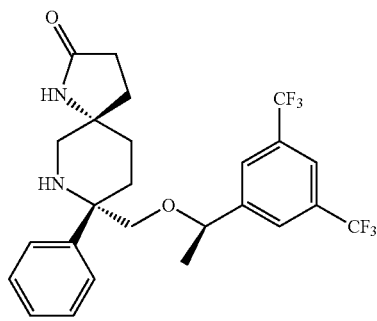

Formula I

The compounds described in the '320 patent are classified as tachykinin compounds, and are antagonists of neuropeptide neurokinin-1 receptors (herein, "NK-1" receptor antagonists). Other $NK_1$ receptor antagonists and their synthesis have been described, for example, those described in Wu et al, *Tetrahedron* 56, 3043-3051 (2000); Rombouts et al, *Tetrahedron letters* 42, 7397-7399 (2001); and Rogiers et al, *Tetrahedron* 57, 8971-8981 (2001) and in published international application no. WO05/100358, each of which are incorporated herein in their entirety by reference.

"NK-1" receptor antagonists have been shown to be useful therapeutic agents, for example, in the treatment of pain, inflammation, migraine, emesis (vomiting), and nociception. Among many compounds disclosed in the above-mentioned '320 patent are several novel diazaspirodecan-2-ones, including the compound of Formula I, which are useful in the treatment of nausea and emesis associated with chemotherapy treatments (Chemotherapy-induced nausea and emesis, CINE).

The synthesis method for preparing the compound of Formula I described in the '320 patent generally follows Scheme I in the provision of 8-[{1-(3,5-Bis-(trifluoromethyl)phenyl)-ethoxy}-methyl]-8-phenyl-1,7-diaza-spiro[4.5]decan-2-one compounds.

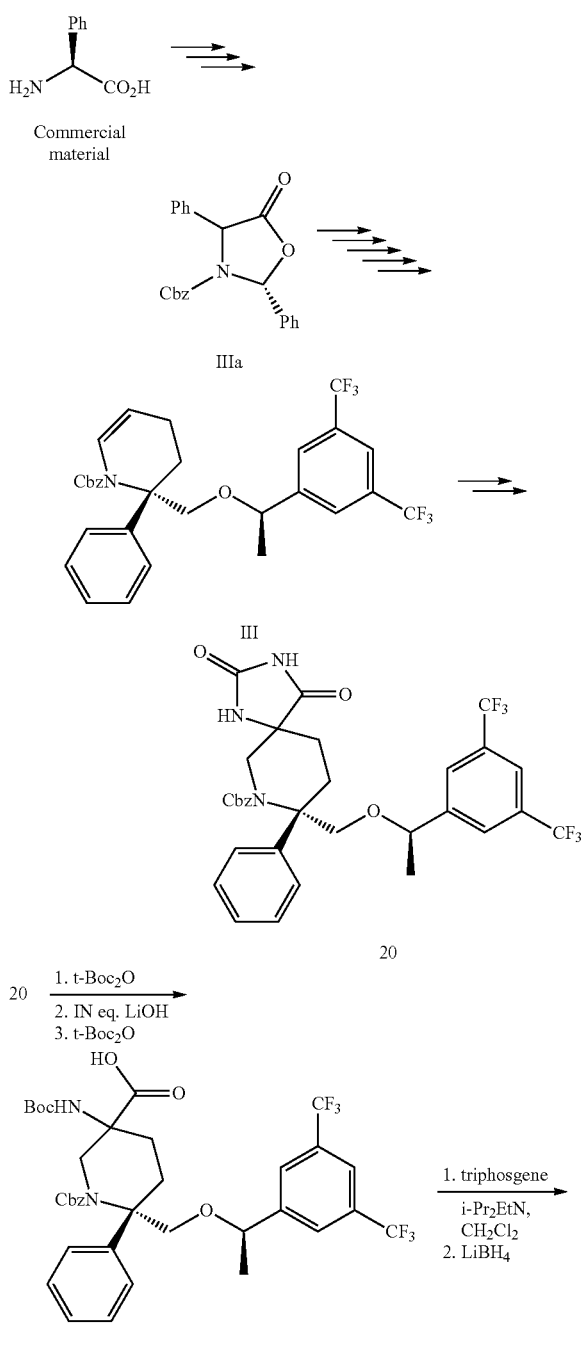

Scheme I

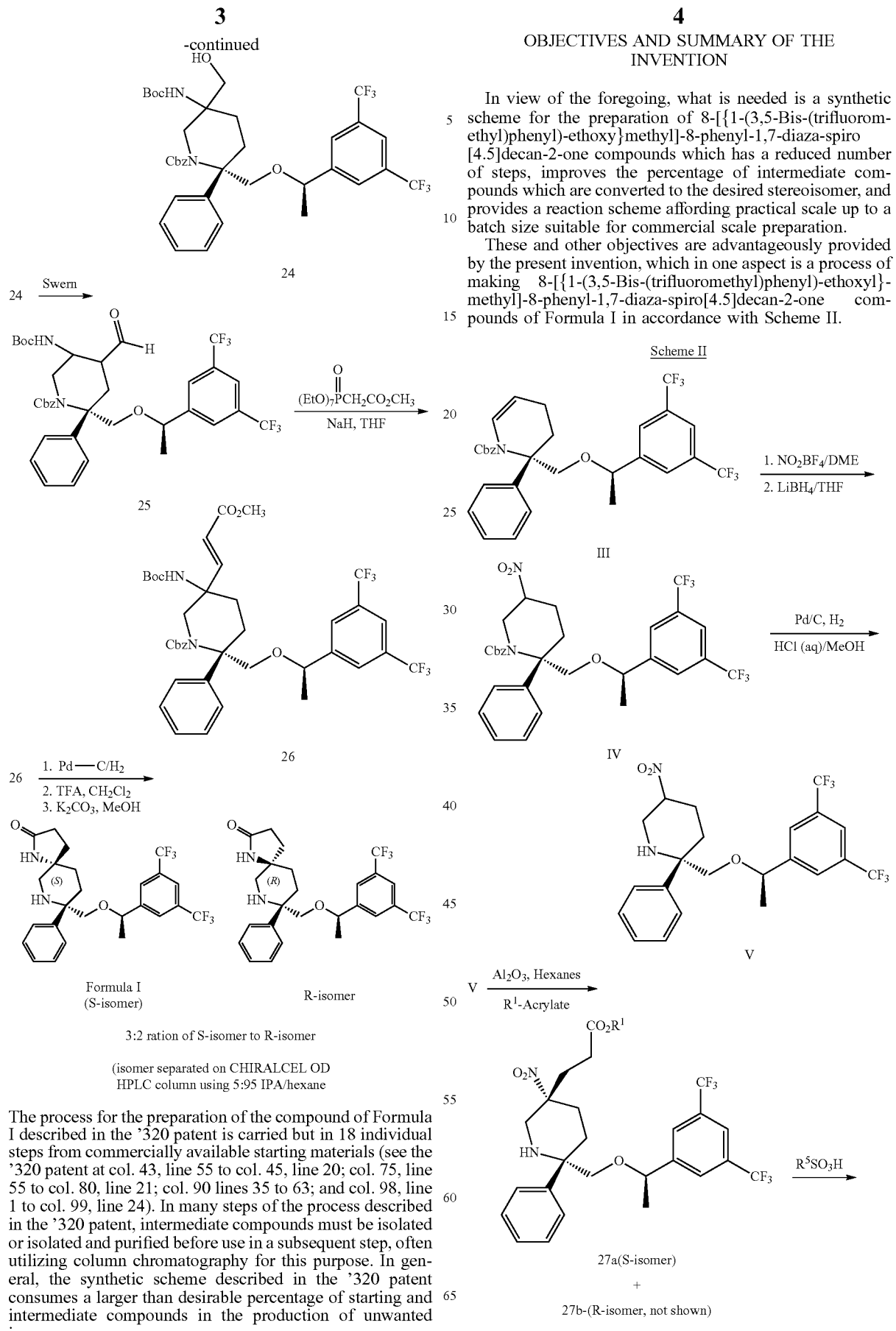

OBJECTIVES AND SUMMARY OF THE INVENTION

In view of the foregoing, what is needed is a synthetic scheme for the preparation of 8-[{1-(3,5-Bis-(trifluoromethyl)phenyl)-ethoxy}methyl]-8-phenyl-1,7-diaza-spiro[4.5]decan-2-one compounds which has a reduced number of steps, improves the percentage of intermediate compounds which are converted to the desired stereoisomer, and provides a reaction scheme affording practical scale up to a batch size suitable for commercial scale preparation.

These and other objectives are advantageously provided by the present invention, which in one aspect is a process of making 8-[{1-(3,5-Bis-(trifluoromethyl)phenyl)-ethoxyl}-methyl]-8-phenyl-1,7-diaza-spiro[4.5]decan-2-one compounds of Formula I in accordance with Scheme II.

The process for the preparation of the compound of Formula I described in the '320 patent is carried but in 18 individual steps from commercially available starting materials (see the '320 patent at col. 43, line 55 to col. 45, line 20; col. 75, line 55 to col. 80, line 21; col. 90 lines 35 to 63; and col. 98, line 1 to col. 99, line 24). In many steps of the process described in the '320 patent, intermediate compounds must be isolated or isolated and purified before use in a subsequent step, often utilizing column chromatography for this purpose. In general, the synthetic scheme described in the '320 patent consumes a larger than desirable percentage of starting and intermediate compounds in the production of unwanted isomers.

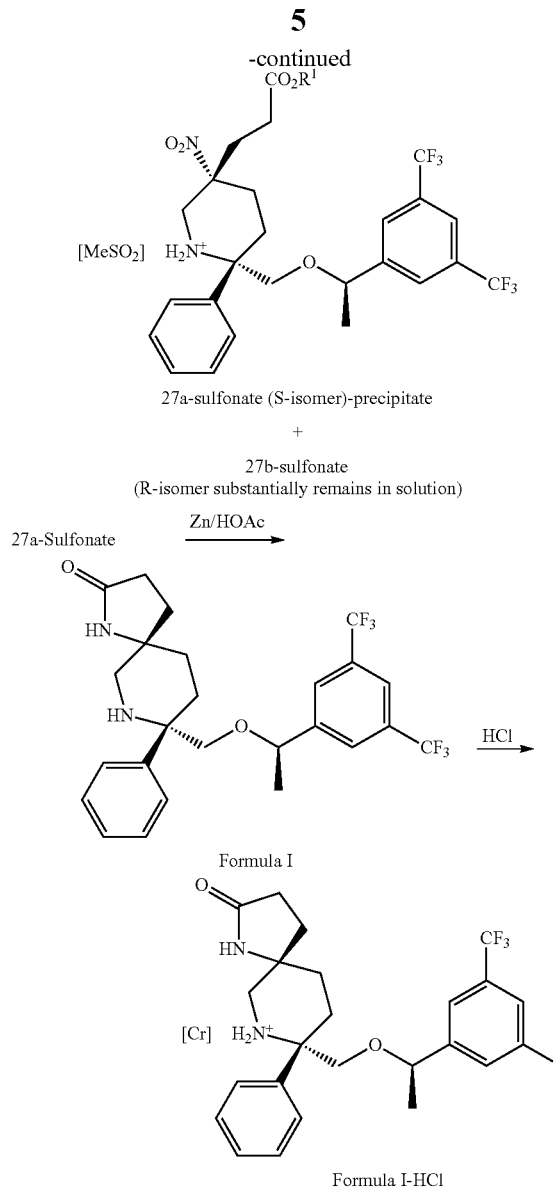

the process comprising:
(a) reacting the protected enamine of Formula III with a nitrating agent to form the corresponding protected nitro-enamine and subsequently reducing the product to a protected piperidine of Formula IV;
(b) deprotecting the protected piperidine of Formula IV from step "a" by reacting it with hydrogen in the presence of a palladium catalyst to form the compound of Formula V;
(c) alkylating the compound of Formula V by reacting it with a Michael acceptor under Michael addition conditions with an acrylate to form the compounds of Formulae 27a and 27b;
(d) selectively precipitating a sulfonate salt of the free base compound of Formula 27a formed in alkylating Step "c" by reacting the reaction mixture from Step "c", containing the compound of Formula 27a, with a sulfonic acid of the formula $R^5$—$SO_3H$ to form the precipitate of Formula 27a-sulfonate;
(e) reducing and cyclizing the compound of Formula 27a-sulfonate to form the lactam of Formula I; and
(f) optionally, precipitating a hydrochloride salt form of the compound of Formula I by reacting the free-base compound of Formula I with HCl.

One aspect of the present invention is the provision of a process for synthesizing the lactam compound of Formula I, the process comprising reducing and cyclizing the compound of the Formula 27a-sulfonate in a one-pot reaction. In some embodiments, it is preferred to carry out the reaction by treating the compound of Formula 27a-sulfonate with acetic acid in the presence of zinc metal. In some embodiments, preferably the compound of Formula 27a is dissolved in concentrated acetic acid and the solution is introduced into a zinc powder/acetic acid suspension. Without wanting to be bound by theory, it is believed that the reaction conditions provided by the zinc metal/acetic acid reaction environment first reduce the nitro group to an amino-group and then form the lactam by acid-catalyzed displacement of the acyl portion of the ester group, thereby cyclizing the compound of Formula 27a and forming the lactam of Formula I.

Another aspect of the present invention is the provision of compound of Formula 27a from the compound of Formula V using a Michael addition reaction yielding at least about 60% of the compound of Formula 27a based on the amount of the compound of Formula V employed. In some embodiments it is preferred to select a basic alumina to carry out the Michael addition. In some embodiments it is preferred to select the acrylate used as a Michael acceptor from in step "c" from acrylates having the structure of the compound of Formula 28a:

Formula 28a wherein $R^1$ is a linear, branched, or cyclic alkyl having up to 6 carbon atoms, phenyl, 2-methoxy-ethyl, 2-(dimethylamino)ethyl, (L)-menthyl, (D)-menthyl, dimethylamide, (R)-benzyl-oxazolidinonamide, (S)-benzyl-oxazolidinonamide, isobornyl, cis-pinan-2-yl, isopinocampheyl, adamantylmethyl, 2-adamantyl, 1-adamantyl, and (−)-8-phenylmenthyl, more preferably $R^1$ is selected from methyl, (−)-8-phenylmenthyl, isobornyl, 1-adamantanyl, 2-adamantanyl, adamantane methanyl, and (+)-isopinocamphenyl, more preferably $R^1$ is selected from methyl and isobornyl. In some embodiments it is preferred to carry out the Michael addition using basic alumina, more preferably a basic alumina with Brockman activity level IV. In some embodiments ft is preferred to carry out the Michael addition using an $R^1$-aerylate Michael acceptor wherein "$R^1$" is selected from methyl- and -isobornyl, more preferably $R^1$ is methyl.

In some embodiments, in Step "d", precipitation step, it is preferred to employ a sulfonic acid of the formula $R^5$—$SO_3H$ or oxalic acid, for example, methylsulfonic acid, to precipitate the sulfonate salt of the compound of Formulae 27a-sulfonate. In some embodiments it is preferred to select $R^5$ from, methyl, alkyl, benzyl, and p-tolyl, more preferably $R^5$ is methyl.

Other aspects and advantages of the invention will become apparent from following Detailed Description.

DETAILED DESCRIPTION OF THE INVENTION

Terms used in the general schemes herein, in the examples, and throughout the specification, include the following abbreviations, together with their meaning, unless defined otherwise at the point of their use hereinafters: Me (methyl); Bu (butyl); t-Bu (tertiary butyl); Et (ethyl); Ac (acetyl); t-Boc or t-BOC (f-butoxycarbonyl); DMF (dimethylformamide); THF (tetrahydrofuran); DIPEA (diisopropylethylamine); MTBE (methyltertiarybutyl ether); RT (room temperature, generally 25° C.); TFA (trifluoroacetic acid); TEA (triethyl amine).

As used herein, the following terms, unless otherwise indicated, are understood to have the following meanings:

The term "substituted" means that one or more hydrogens on the designated atom or group of atoms in a structure is replaced with a selection from the indicated group, provided that the designated atom's normal valency under the existing circumstances is not exceeded, and that the substitution results in a stable compound. Combinations of substituents and/or variables are indicated when such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

"Patient" includes both humans and animals.

"Mammal" means humans and other mammalian animals.

"Alkyl" means an aliphatic hydrocarbon group which may be linear straight or branched and comprising about 1 to about 10 carbon atoms in the chain. Branched means that one or more lower alkyl groups such as methyl, ethyl or propyl, are attached to a linear alkyl chain. Non-limiting examples of suitable alkyl groups include methyl, ethyl, n-propyl, isopropyl, n-butyl, t-butyl and n-pentyl.

"Alkenyl" means an aliphatic hydrocarbon group containing at least one carbon-carbon double bond and which may be straight or branched and comprising about 2 to about 10 carbon atoms in the chain. Branched means that one or more lower alkyl groups such as methyl, ethyl or propyl, are attached to a linear alkenyl chain. Non-limiting examples of suitable alkenyl groups include ethenyl, propenyl, n-butenyl, 3-methylbut-2-enyl and n-pentenyl.

"Alkylene" means a difunctional group obtained by removal of an additional hydrogen atom from an alkyl group, as "alkyl" is defined above. Non-limiting examples of alkylene include methylene (i.e., —CH$_2$—), ethylene (i.e., —CH$_2$—CH$_2$—) and branched chains, for example, —CH(CH$_3$)—CH$_2$—.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Cycloalkyl" means a non-aromatic mono- or multicyclic ring system comprising about 3 to about 10 carbon atoms, preferably about 3 to about 6 carbon atoms. Non-limiting examples of suitable monocyclic cycloalkyls include cyclopropyl, cyclobutyl, cyclopentyl, cyclohexyl, cycloheptyl and the like. Non-limiting examples of multicyclic cycloalkyls include, but are not limited to 1-decalin, norbornyl and cognitors, adamantyl and cognitors.

"Halo" means a halogen selected from fluoro, chloro, bromo, or iodo groups.

"Aminoalkyl" means an alkyl as defined above having at least one hydrogen atom on the alkyl moiety replaced by an amino functional (i.e., —NH$_2$) group. Alkylamino means an amino functional group having one or both hydrogens replaced by an alkyl functional group, as "alkyl" is defined above.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art.

A wavy line ~~~ appearing on a structure and joining a functional group to the structure in the position of a bond generally indicates a mixture of, or either of, the possible isomers, e.g., containing (R)- and (S)-stereochemistry. For example.

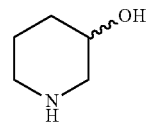

means containing either, or both of

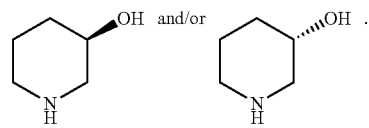 [SMILES: O[C@@H]1CCCNC1 ; O[C@H]1CCCNC1]

A wavy line which terminates a bond indicates that the portion of the structure depicted is attached to a larger structure at the indicated bond, for example,

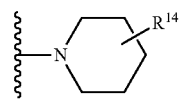

implies that the nitrogen of the substituted piperidyl group depicted is bonded to an undepicted structure on which it is a substituent.

Lines drawn into ring systems, for example the substituted aryl group;

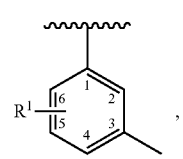

indicates that a substituent (R$^1$) may replace a hydrogen atom of any of the ring carbons otherwise bonded to a hydrogen atom. Thus, as illustrated, R$^1$ can be bonded to any of carbon atoms 2, 4, 5, or 6, but not 3, which is bonded to a methyl substituent, or 1, through which the substituted aryl group is bonded.

As well known in the art, a bond draw from a particular atom wherein no moiety is depicts at the terminal end of the bond indicates a methyl group bound through that bond to the atom, unless stated otherwise. For example:

represents 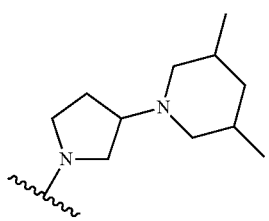 [SMILES: *N1CCC(N2CC(C)CC(C)C2)C1]

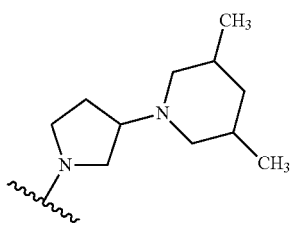

However, sometimes in the examples herein, the CH₃ moiety is explicitly included in a structure. As used herein, the use of either convention for depicting methyl groups is meant to be equivalent and the conventions are used herein interchangeably for convenience without intending to alter the meaning conventionally understood for either depiction thereby.

The term "isolated" or "in isolated form" for a compound refers to the physical state of said compound after being isolated from a process. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

When any variable (e.g., aryl, heterocycle, $R^2$, etc.) occurs more than one time in any constituent or in a formula, its definition on each occurrence is independent of its definition at every other occurrence.

As mentioned above, a process for preparing the compound of Formula I from the compound of Mia via intermediate compound of Formula III is described in the '320 patent.

Formula IIIa

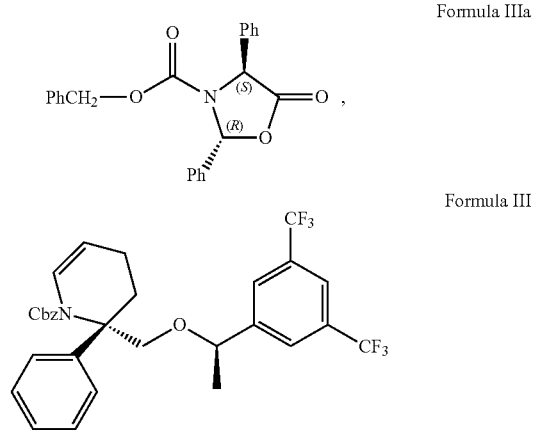

Formula III

Preparation of the compound of Formula IIIa from commercially available (S)-α-phenylglycine is described by M. J. O'Donnel; Z. Fang; X. Ma; and J. C. Huffman in "NEW METHODOLOGY FOR THE SYNTHESIS OF α,α-DI-ALKYLAMINO ACIDS USING THE 'SELF-REGENERA-TION OF STEREOCENTERS' METHOD: α-ETHYL-α-PHENYLGLYCINE". Heterocycles, Vol 46, 1997, pp 617 to 630, (see pages 618 through 619 therein), which is incorporated herein by reference in its entirety.

In the process described in the '320 patent for the preparation of the compound of Formula I, the compound of Formula III is converted to the compound of Formula IIIb (in two steps by oxidation of a corresponding alcohol intermediate). Compound IIIb is then converted in one step to the compound of Formula 20 shown in Scheme I above. Accordingly, the '320 patent describes preparation of the compound of Formula I from the compound of Formula III in 13 individual process steps.

Formula IIIb

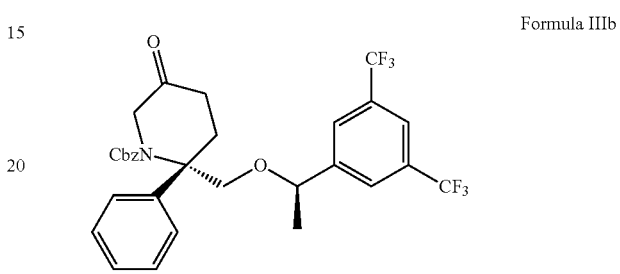

The inventors have surprisingly found that the compound of Formula I can be prepared, as shown in Scheme II, below, from the compound of Formula III in 4 process steps. Accordingly, the process of the present invention eliminates at least half of the number of steps employed in previous preparation processes. Moreover, as will be described below, various of the steps of the present invention process provide improved yield of intermediate compounds for an overall increase in the amount of the compound of Formula I provided from a given amount of the compound of Formula III initially employed in the process. As shown in Scheme II, the compound of Formula III utilizes benzyl carbamate as a protecting group for the enamine nitrogen. It will be appreciated that other protecting groups may alternatively be employed and still be within the scope of the present invention.

Scheme II

Step a-Nitration

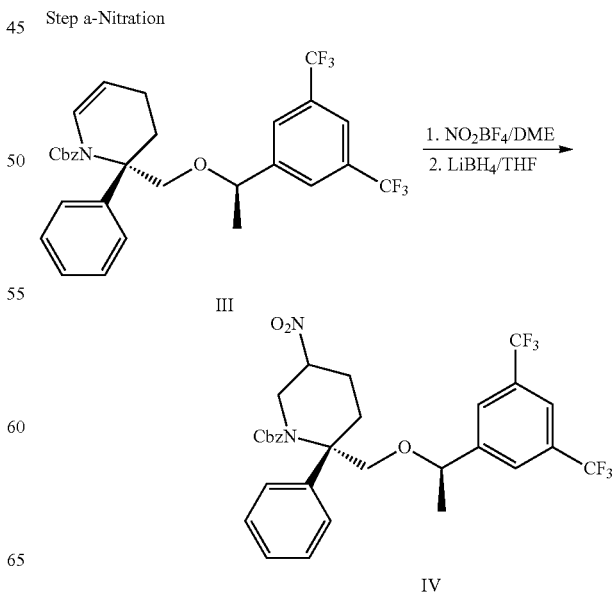

11

Step b-Deprotection

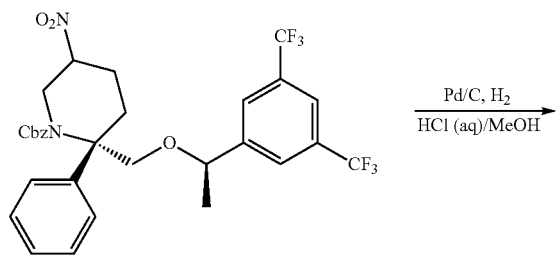

IV

Step c-Alkylation

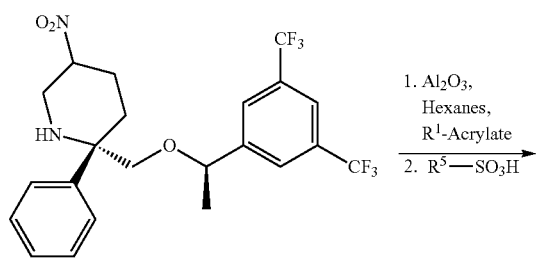

V

Step d-Lactam Formation

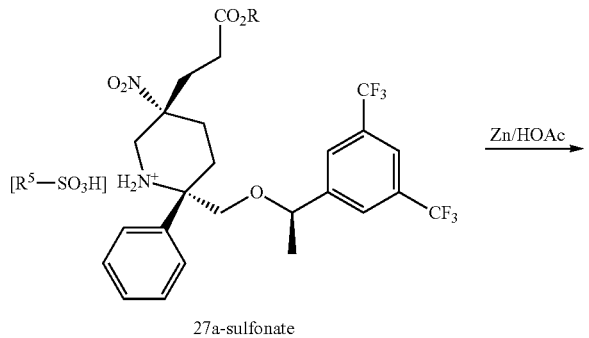

27a-sulfonate

12

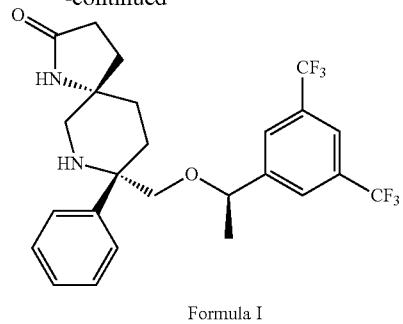

Formula I

Optionally, after Step "d", the compound of Formula I can be precipitated from the reaction mixture as a salt by treatment of the reaction mixture workup with an acid. Accordingly, in some embodiments it is preferred to react the free-base compound of Formula I present in the reaction workup with an acid, for example, HCl, to precipitate a salt form of the compound of Formula I, for example, a hydrochloride salt form. Next, each step of the process of Scheme II will be described in greater detail.

Nitration Step

Step "a" of the process of the present invention, provision of the nitro-substituted intermediate compound of Formula IV from the corresponding enamine compound of Formula III, can be carried out in accordance with Scheme IIa, wherein the substrate is first nitrated and then the double bond of the six-membered ring is reduced.

Scheme IIa

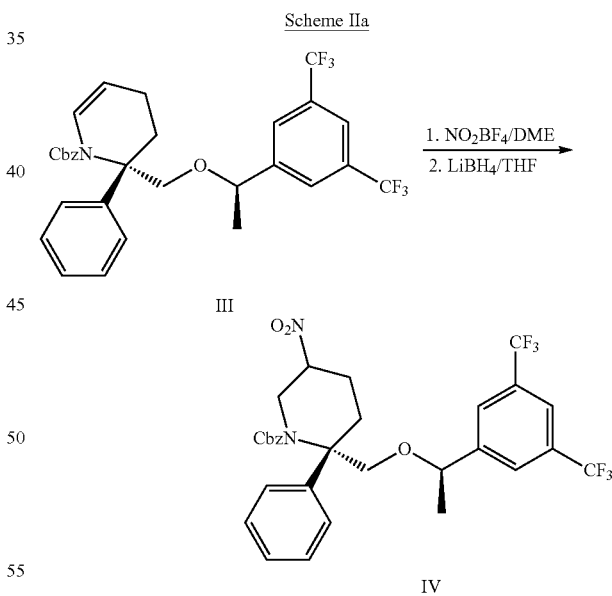

In general, nitration is carried out in a non-protic, low polarity solvent, for example THF and DME using a nitrating reagent, for example nitronium tetrafluoroborate (nitronium-TFB), optionally in the presence of potassium phosphate tribasic. In some embodiments it is preferred to run the reaction without $K_3PO_4$ in the reaction mixture and thereby minimize impurities which may otherwise be formed when $K_3PO_4$ is present in the reaction mixture. In some embodiments it is preferred to carry out the nitration using nitronium-TFB in DME (in which nitronium-TFB has acceptable solubility). Nitration of the compound of Formula III using nitronium-TFB in THF solvent is described in published international application no. WO05/100358 (the '358 publication), albeit not in the course of synthesizing the compound of Formula I (see the '358 publication, page 66, step "a" of preparative Example 5). The '358 publication is incorporated herein by reference in its entirety. Once the nitrated intermediate compound has been prepared, it may be used as prepared in the reaction workup directly in subsequent steps, or optionally, isolated from the reaction workup prior to using in subsequent steps.

Following nitration, the nitrated compound is treated with a hydride reducing agent, for example lithium borohydride and sodium borohydride, to reduce the protected enamine double bond of the nitrated intermediate to yield the compound of Formula IV. In some embodiments using DME as the solvent in which the compound of Formula III is nitrated, it is preferred to strip off the reaction solvent by distillation and replace it with THF prior to carrying out the reduction step. This provides the nitrated intermediate in a solvent suitable for carrying out the reduction with a metal hydride without the need to isolate the nitrated intermediate. In some embodiments, it is preferred to carry out the reduction using lithium borohydride in THF.

Although it is preferred to use the above-described method for the preparation of the compound of Formula IV, it will be appreciated that other means may be selected to prepare the compound of Formula IV for use in the process of Scheme II and be within the scope of the present invention.

Step b—Deprotection

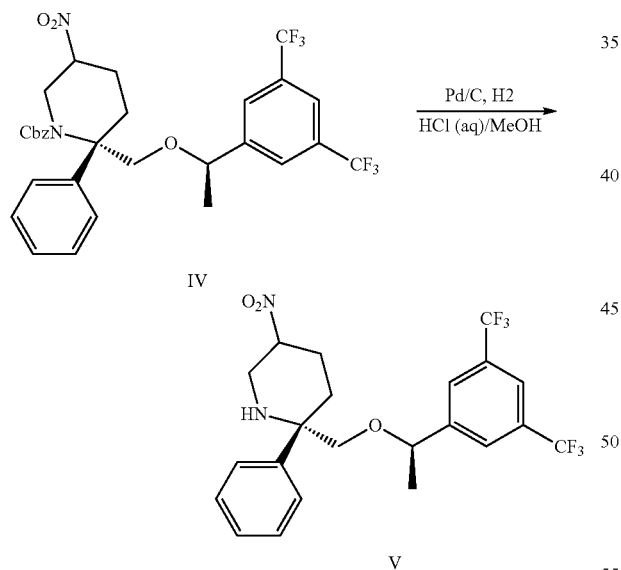

IV

Step "b" of the present invention process, deprotection of the piperidine nitrogen in the compound of Formula IV to yield the compound of Formula V, can be carried out using metal-catalyzed hydrogenation or by treating the intermediate of Formula IV under acid conditions. Examples of suitable acid deprotection conditions include, but are not limited to trifluoroacetic acid (TFA) and a mixture of HBr/acetic acid. It will be appreciated that other deprotection schemes may also be employed, for example, iodotrimethylsilane (TMS-iodide) and deprotection using thiols. The inventors have surprisingly found that when TMS-iodide is employed, the byproduct benzyliodide can be efficiently trapped with triphenylphoshine to suppress benzylamine formation with the piperidine nitrogen of the deprotected product. In some embodiments it is preferred to use hydrogen and a hydrogenation catalyst, for example, a palladium metal catalyst, to mediate the deprotection reaction in Step "b", more preferably the catalyst employed is Pd supported on carbon black. In some embodiments it is preferred to carry out deprotection in an alcohol solvent, for example, methanol. In some embodiments, it is preferred to work up the previous reduction step by adding methanol and distilling off the reaction solvent until suitably concentrated, and using the crude concentrated methanol solution directly in the subsequent deprotection reaction.

Step c—Alkylation

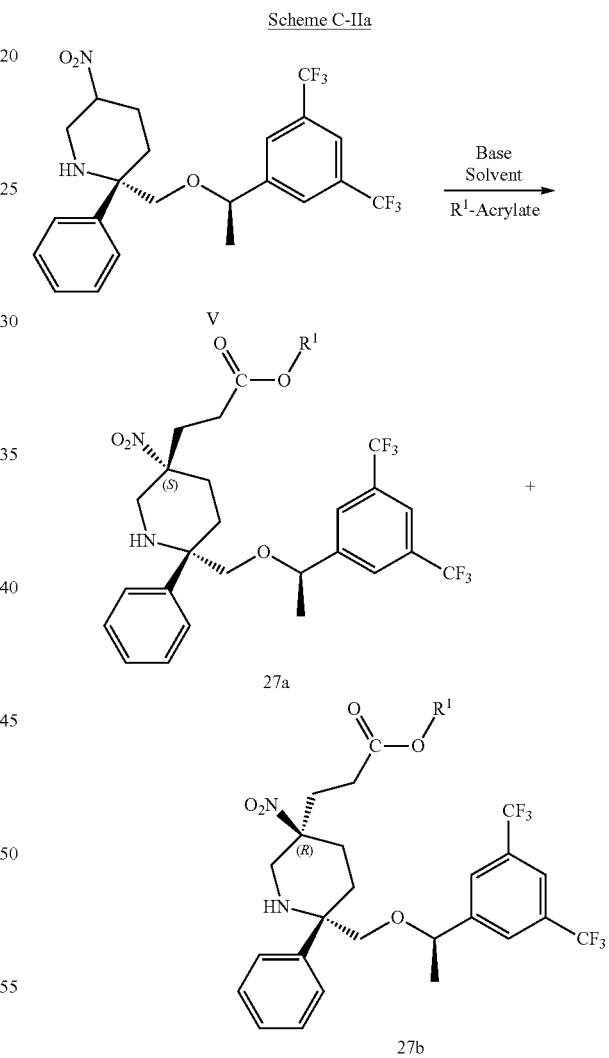

After the deprotection step "b", the piperidine of Formula V is coupled to an acrylate under base-catalyzed Michael addition conditions. In some embodiments it is preferred to carry out the Michael addition in a solvent selected from n-hexane, MTBE, cyclohexane, toluene, methanol, dimethyl formamide (DMF), and THF. In some embodiments it is preferred for the solvent to be n-hexane. In some embodiments, the reaction mixture from the deprotection step "b"

is worked up by successive additions of toluene, followed by azeotropic distillation, and then successive additions of n-hexane, followed by distillation maintaining the still pot between 30° C. and 60° C. until distillation ceases, thus, the residual mixture will have the lowest possible volume at this still temperature. In some embodiments it is preferred to employ the resulting concentrate directly in the Michael addition step which follows. Step "c".

In some embodiments it is preferred to select a Michael acceptor from compounds having the structure of Formula 28a:

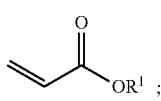

Formula 28a wherein "R¹" is selected from alkyl, cycloalkyl (including multicyclicalkyls), and aryl, more preferably "R¹" is selected from methyl, t-butyl, phenyl, 2-methoxy-ethyl, 2-(dimethylamino)ethyl, (L)-menthyl, (D)-Menthyl, Dimethylamide, (R)-Benzyl-oxazolidinonamide, (S)-benzyl-oxazolidinonamide, isobornyl, cis-pinan-2-yl, isopinocampheyl, adamantylmethyl, 2-adamantyl, 1-adamantyl, and (−)-8-phenylmenthyl, more preferably R is selected from methyl, (−)-8-phenylmenthyl, isobornyl, 1-adamantanyl, 2-adamantanyl, adamantane methanyl, and (+)-isopinocampheyl, more preferably R¹ is methyl.

In some embodiments it is preferred to carry out the Michael addition reaction in the presence of a base. In some embodiments the base is selected from: an organic base, for example, a homogeneous base, for example triethylamine, and a heterogeneous base, for example, basic polymer resin having amine functionality, for example Amberlyst A-21® from Rohm and Haas; and a heterogeneous, inorganic base, for example an aluminum oxide (neutral or basic), a metal alkoxide (for example. Mg(OEt)₂, and magnesium oxide. In some embodiments it is preferred to employ a basic aluminum oxide to catalyze the Michael addition reaction, more preferably, basic aluminum oxide having a Brockman activity of I, II, III, or IV, available as an article of commerce, more preferably a basic aluminum oxide having a Brockman activity of IV having a 5 wt. % to 10 wt. % water content.

Several metal oxides have been found useful for catalyzing the Michael addition reaction, for example, magnesium oxide (MgO) and aluminum oxide (alumina). It will be appreciated that the Michael addition reaction can result in two different isomers being produced, shown in the reaction Scheme C-IIa as the compounds of Structures 27a (S-isomer, desired isomer) and 27b (R-isomer, an undesired isomer). Although the ratio of the isomers produced in the Michael addition reaction can be varied by altering the reaction solvent, the steric demand of the Michael acceptor, and other reaction conditions, the inventors have surprisingly found that the choice of base can greatly influence the ratio of S-isomer to R-isomer produced in the addition reaction. The inventors have surprisingly found that magnesium oxide base produces proportionately more of the R-isomer than the desired S-isomer. Additionally, the inventors have surprisingly found that the use of basic alumina as a base in the Michael addition reaction selectively produces more of the desired S-isomer over the R-isomer. Moreover, the inventors have surprisingly found that selecting Bockman activity level IV basic alumina as the base in the Michael reaction produces substantially more of the S-isomer than R-isomer, for example, using basic alumina of activity level IV, the inventive process can produce a reaction product with a ratio of S-isomer to R-isomer that exceeds 3:1 (75% S-isomer) even when it is used in reactions employing a sterically undemanding Michael acceptor, for example, methyl acrylate.

Moreover, the inventors have found that the inventive Michael addition reaction, when run with both a base providing maximum yield of the desired isomer, and employing a sterically demanding Michael acceptor, provides a reaction product comprising in some embodiments from about 84% to about 86% of the S-isomer, and in some embodiments up to about 90% S-isomer. Suitable sterically demanding Michael acceptors are, for example, compounds containing a bornyl structure and compounds containing an adamantly structure. Additional examples of suitable sterically demanding Michael acceptors include, but are not limited to, with reference to the structure of Compound 28a (above), compounds wherein the "R¹" group is selected from:

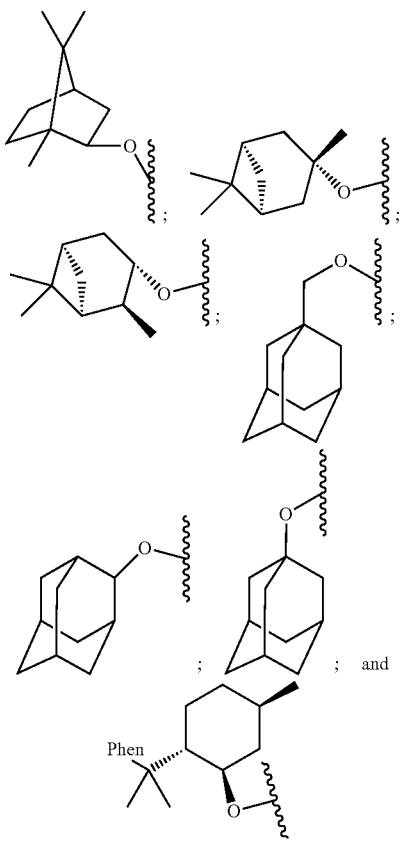

which are isobornyl, cis-pinan-2-yl, (+)-isopinocampheyl, adamantly-methyl, 2-adamantyl, 1-adamantyl, and (−)-8 phenylmenthyl substituents, respectively.

In some embodiments, to maximize the amount of desirable "S-isomer" produced in the Michael addition reaction it is preferred to use n-hexane for the reaction solvent, select aluminum oxide (basic) having Brockman activity level IV as the base catalyst, and use isobornylacrylate as a Michael acceptor (thus "R¹" is isobornyl-).

The inventive Michael addition reaction can be carried out using the compound of Formula IV (the protected precursor to the compound of Formula V, see for example, deprotection Step B, above) to provide an acylated product which, upon deprotection of that product in accordance with deprotection Step "b", yields the compounds of Formula 27a and Formula 27b. Accordingly, the compound of Formula I can be produced by reversing the order of deprotection step b and alkylation step c. However, the inventors have surprisingly found that when used in the alkylation Step "c", the protected compound of Formula IV yields a greater proportion of the undesirable R-isomer compound of Formula 27b relative to the amount of desired S-isomer compound of Formula 27a formed in the inventive Michael addition reaction under substantially the same reaction conditions as were used for carrying out the inventive Michael addition using the compound of Formula V (deprotected compound). Accordingly, to maximize the amount of the desired S-isomer compound of Formula 27a provided by the inventive Michael addition in the alkylation step, it is preferred to deprotect the compound of Formula IV first to form the compound of Formula V and then carry out the alkylation step rather than carry out the alkylation step on the compound of Formula IV and deprotect the product to provide the compound of Formula 27a.

In some embodiments, the product of the Michael addition is preferably isolated as a solution of the product by filtering the reaction mixture to remove solids and concentrating the solution under vacuum. In some embodiments, preferably the concentrated solution is then reacted directly with a sulfonic acid of the formula $R^5$—$SO_3H$ or oxalic acid, where $R^5$ is selected from methyl, benzyl, and p-toluyl groups, to provide the ester compound of Formula 27a as a crystalline precipitated sulfonate salt of Formula 27a-sulfonate, see Scheme C-IIb (where $R^5$ is a methyl group, thus, the methylsulfonate salt is precipitated). It will be appreciated that other salts, including other sulfonate salts, may be precipitated without departing from the scope of the invention.

Although some amount of the unwanted "R" isomer is coprecipitated with the desired isomers of Formula 27a (27b-sulfonate), the precipitation in accordance with Scheme C-IIb provides a solid comprising substantially the compound of Formula 27a-sulfonate. In some embodiments precipitation using Scheme C-IIb provides a precipitated material containing more than about 96% the compound of Formula 27a-sulfonate (S-isomer) with less than 4% of the undesirable compound of Formula 27b-sulfonate (unwanted R-isomer) precipitated.

Scheme C-IIb

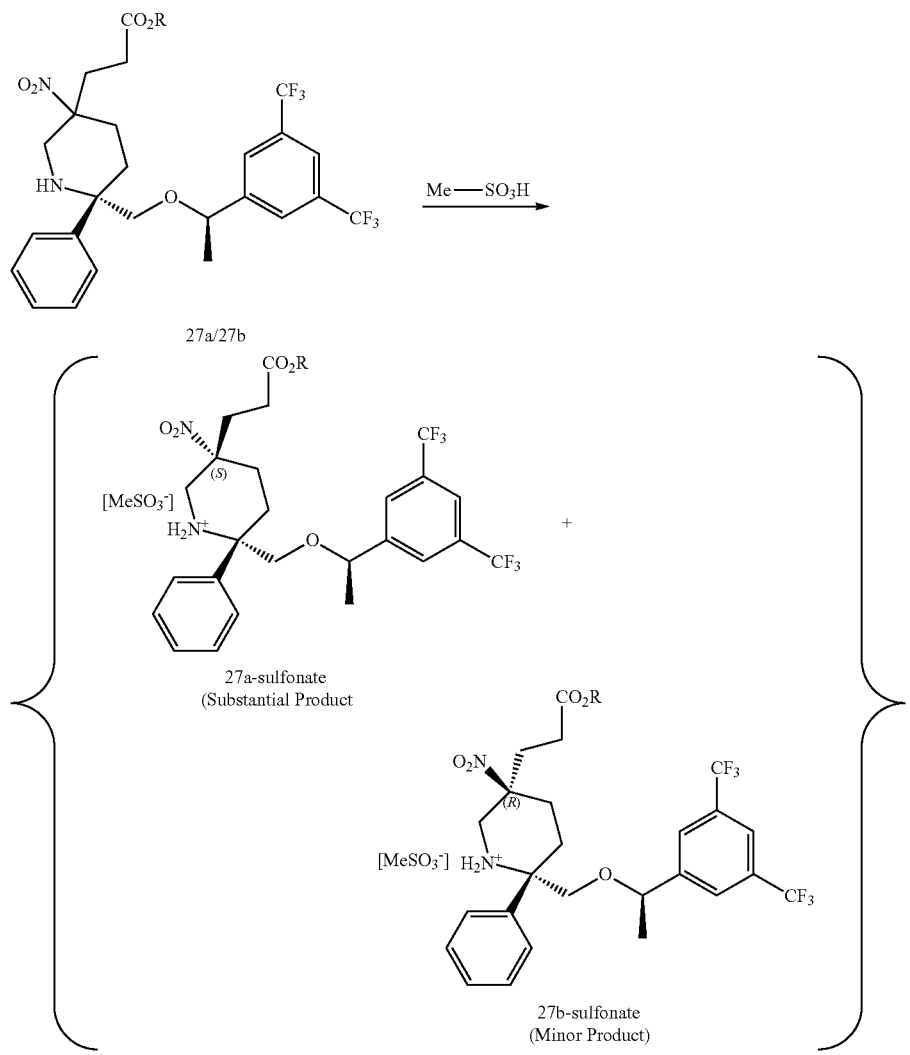

With reference to Scheme C-IIb, in some embodiments it is preferred to precipitate the methane sulfonate salt of the free-base compound as a crystalline material from the reaction mixture prepared above by treating the reaction mixture in a suitable solvent (for example, MTBE, or a mixed solvent, for example, toluene and isopropanol) with an excess of methanesulfonic acid, and crystallizing the resulting methansulfonate salt from the mixture, either by cooling, seeding the mixture, or a combination of the two. In some embodiments it is preferred to avoid using an alcohol solvent to suppress ester exchange reactions in the product which could lead to the formation of unwanted impurities. The precipitate is preferably isolated by vacuum filtration for use in the subsequent lactam formation step "d".

Step d—Lactam Formation

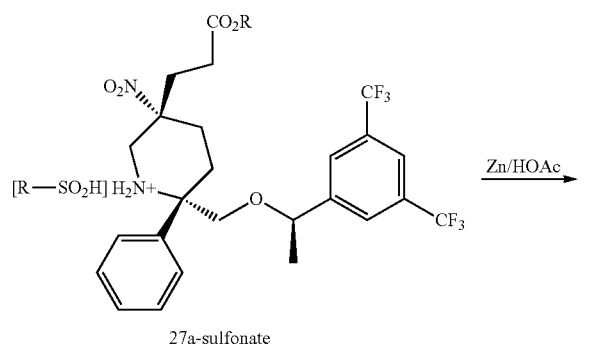

27a-sulfonate

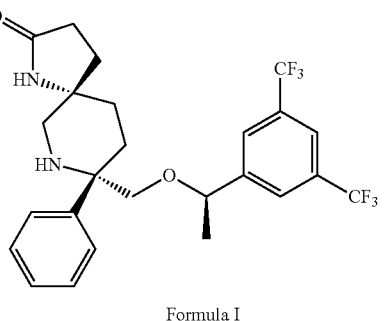

Formula I

Formation of the lactam of Formula I from the compound of Formula 27a-sulfonate is carried out by treating the sulfonate salt formed in alkylation step "c" (containing substantially only the compound of Formula 27a-sulfonate) with suitable reagents to effect reduction of the nitro-group with simultaneous, contemporaneous, or sequential cyclization to form the lactam of Formula I. Without wanting to be bound by theory, it is believed that the reaction conditions provided by employing zinc metal and acetic acid results in reduction of the nitro-group of the compound of Formula 27a-sulfonate to the corresponding amine (however transiently) with formation of the lactam of Formula I by intermolecular acylation (using the ester group present) of the newly formed amine, thereby cyclizing the substituents to form the lactam of Formula I. In some embodiments it is preferred to carry out the lactam forming step "d" by reacting the compound of Formula 27a-sulfonate with zinc metal in the presence of acetic acid. In some embodiments it is preferred to dissolve the sulfonate salt from Step "c" in concentrated acetic acid and combine that solution with a suspension of zinc powder in concentrated acetic acid to carry out the lactam-forming reaction.

After formation of the compound of Formula I, optionally, the compound of Formula I is extracted from the reaction mixture into toluene, and the toluene solution is treated with hydrochloric acid to precipitate the hydrochloride salt of the compound of Formula I. In some embodiments it is preferred to recrystallize the hydrochloride salt thus precipitated from mixed ethanol/isopropanol solvent.

In some embodiments, Step d is carried out under conditions in which a substantial portion of the compound of Formula Ia1 is formed.

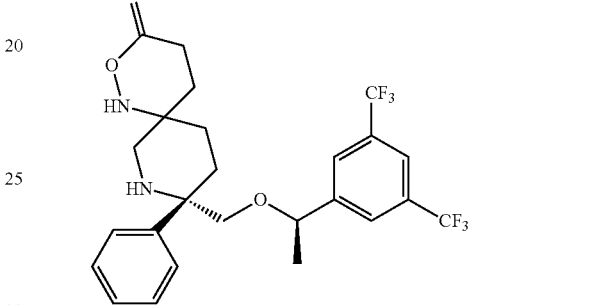

Formula Ia1

When reactor conditions favor slow reduction of the nitro group, for example, when low intensity agitation is used in the reactor, the intermediate formed during reduction of the nitro group has sufficient lifespan to participate in the ring closing reaction in accordance with Scheme IIIa.

Scheme IIIa

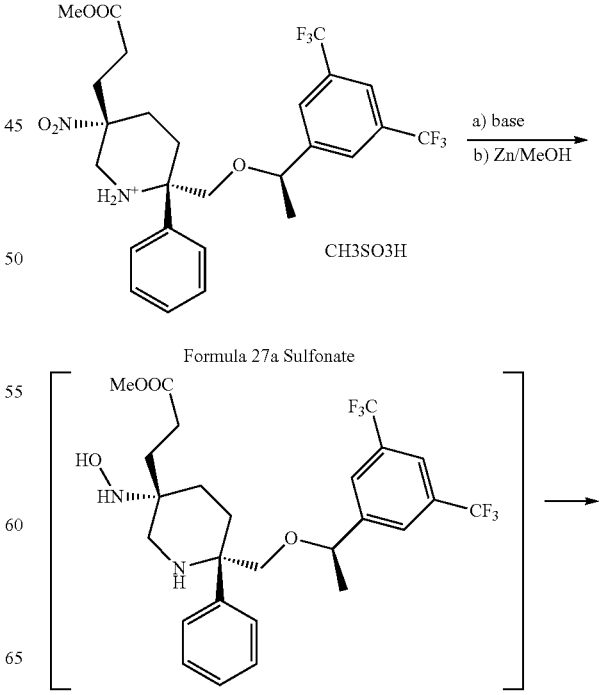

Formula 27a Sulfonate

-continued

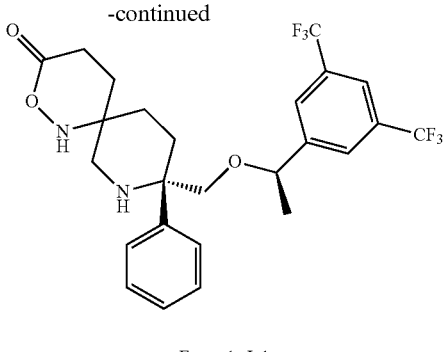

Formula Ia1

Accordingly, the formation of the compound of Formula Ia1 is increased when closing proceeds faster than reduction during the nitro-reduction/lactam formation Step d of the process.

The inventors have surprisingly found that once formed, the Compound of Formula Ia1 can be converted in good yields to the compound of Formula I using Raney nickel as a hydrogenation catalyst to reduce the compound, in accordance with Scheme IIIb shown below.

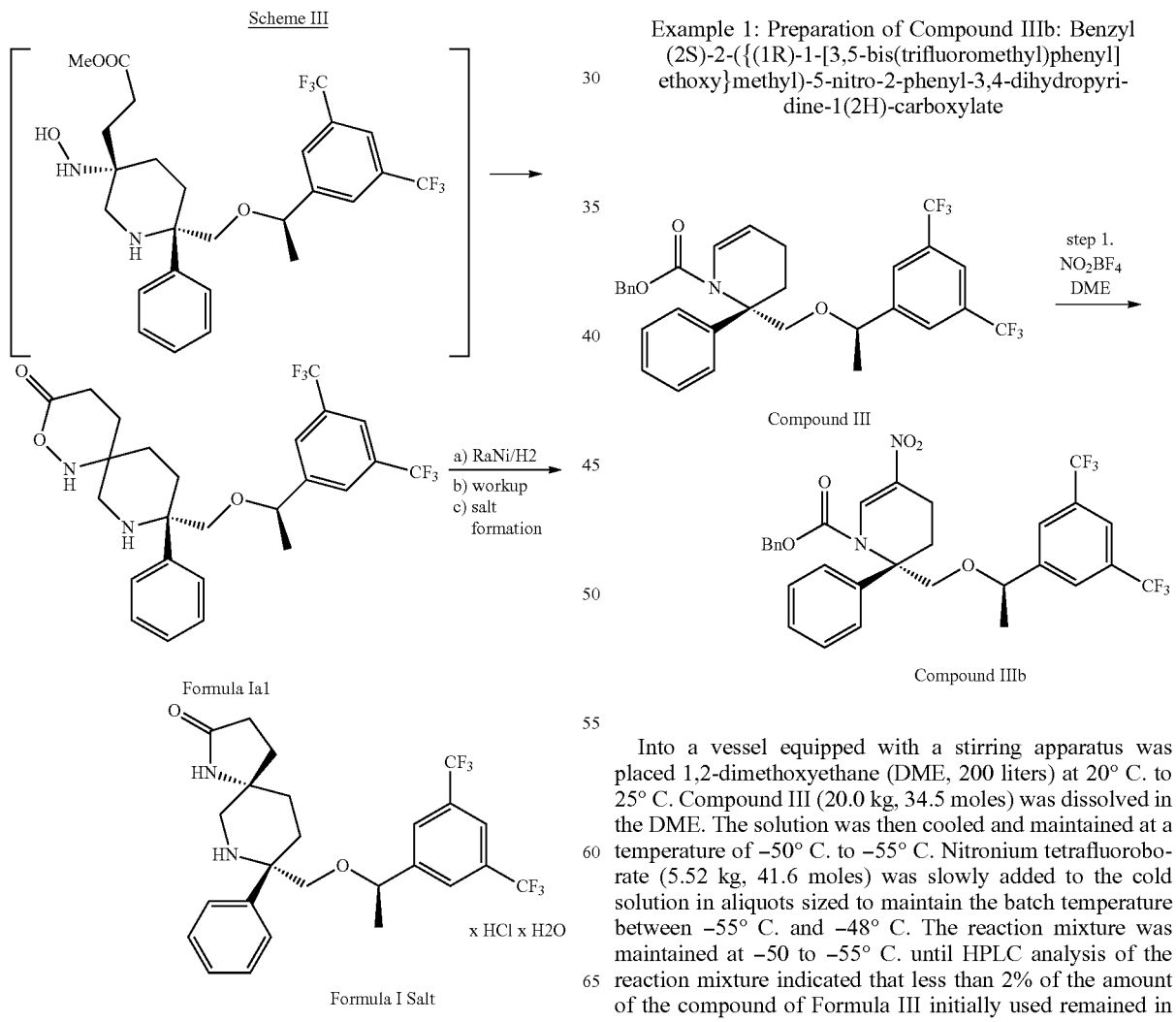

Accordingly, when preparation of the compound of Formula Ia1 is not desired, the product can be converted to the compound of Formula I in good yields by reducing the compound of Formula Ia1 using hydrogen and Raney nickel as a hydrogenation catalyst. When such a reaction is desired, preferably the reaction is carried out at a temperature of about 50° C.

EXAMPLES

Unless otherwise specified, all reagents are articles of commerce, laboratory grade, and used as received. The following solvents and reagents may be referred to by their abbreviations in parenthesis:

tertiary-butoxycarbonyl: t-BOC
tetrahydrofuran: THF
Dimethylformamide: DMF
methyl-tertiarybutyl ether: MTBE
mole: mol.

Following are general and specific methods for the preparation of compounds having formula I, III, IIIb, IV, V, 27a and 27b described above. There follows non-limiting examples illustrative of the present invention but not limiting the present invention.

Example 1: Preparation of Compound IIIb: Benzyl (2S)-2-({(1R)-1-[3,5-bis(trifluoromethyl)phenyl] ethoxy}methyl)-5-nitro-2-phenyl-3,4-dihydropyridine-1(2H)-carboxylate Into a vessel equipped with a stirring apparatus was placed 1,2-dimethoxyethane (DME, 200 liters) at 20° C. to 25° C. Compound III (20.0 kg, 34.5 moles) was dissolved in the DME. The solution was then cooled and maintained at a temperature of −50° C. to −55° C. Nitronium tetrafluoroborate (5.52 kg, 41.6 moles) was slowly added to the cold solution in aliquots sized to maintain the batch temperature between −55° C. and −48° C. The reaction mixture was maintained at −50 to −55° C. until HPLC analysis of the reaction mixture indicated that less than 2% of the amount of the compound of Formula III initially used remained in the reaction mixture.

At the end of the reaction, sodium carbonate solution (12 Kg Na₂CO₃ dissolved in 50 L water) was added while allowing the temperature of the reaction mixture to rise. The reaction mixture temperature was maintained at between −20° C. and 0° C. during the addition of the sodium carbonate solution. After approximately 50 L of sodium carbonate solution had been added, the pH of the mixture was evaluated using pH paper and found to be pH 5.5. Solid sodium carbonate was added until the mixture had a pH of greater than pH 7.0 but not exceeding pH 10. During the addition of sodium carbonate, the temperature of the mixture was maintained between −20° C. and 0° C. When the the pH had been adjusted to a value between pH 7.0 and pH 10, it was warmed to ambient temperature (between 20° C. and 25° C.). After warming, the reaction mixture was filtered and the filter cake washed with DME, which was combined with the filtrate.

The filtrate was concentrated by distilling off the volatiles under vacuum 80 mbar to 150 mbar) to the lowest possible volume while maintaining the filtrate at a temperature between 30° C. and 50° C. Two aliquots of MTBE (20 L each) were added to the concentrate in sequence. After each addition of MTBE to the concentrate, the mixture was again concentrated by distilling under vacuum (from sufficient vacuum to induce boiling up to 520 mbar) to the lowest possible volume while maintaining the filtrate at a temperature between 30° C. and 50° C. After the second distillation, MTBE (60 L) was added to the residue. The mixture was agitated, and permitted to settle, the layers of the mixture were split. The organic layer was washed with water (3 aliquots of 20 L each) and concentrated under vacuum (80 mbar to 200 mbar), to the lowest possible volume while maintaining the organic layer at a temperature between 30° C. and 50° C. THF was added to the concentrate (20 L), and distilled off under vacuum (80 mbarr to 150 mbar) to achieve the lowest possible volume while maintaining the mixture at a temperature between 30° C. and 50° C. A second aliquot of THF was added to the concentrate (60 L) and the water content was determined by Karl Fischer titration to be less than 0.2%. The solution thus obtained was analyzed by HPLC, and the yield of the compound of Formula IIIb was determined to be 90%.

Example 2: Preparation of Compound IV: Benzyl (2S)-2-({(1R)-1-[3,5-bis(tri-fluoro-methyl)-phenyl]ethoxy}methyl)-5-nitro-2-phenylpiperidine-1-carboxylate

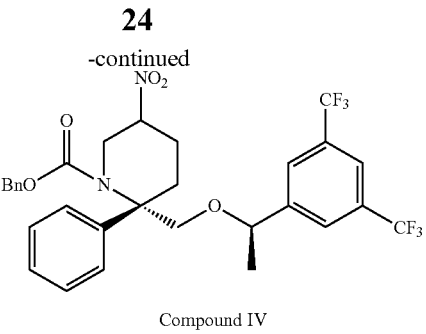

Compound IV

To the reaction mixture comprising the Compound IIIb solution (152.34 kg, 53.3 kg active, 87.6 moles) produced in Example 1 was added tetrahydrofuran (295 liters), and the mixture was cooled and maintained at a temperature between −22° C. to −18° C. A solution of lithium borohydride (7.92 kg, 10% in THF, 35.6 moles) was added to the mixture at a rate permitting the mixture to be maintained at a temperature between −22° C. and −18° C. The reaction was maintained at −22 to −18° C. until HPLC analysis indicated that the reaction was complete. At the completion of the reaction water (104 L) was added at a rate that maintained the temperature of the reaction mixture below 20° C. Concentrated hydrochloric add was added to the mixture until the pH of the mixture was between pH 3.5 and pH 4.5. The mixture was concentrated at 30° C. to 50° C. under vacuum (80 mbar to 120 mbar) until distillation of the solvent ceased. Additional methyl tert-butyl ether (86 L) was added to the concentrated reaction mixture and 43 L distilled off at 30° C. to 50° C. under sufficient vacuum to maintain distillation, reducing the THF level to less than 10 vol. %. MTBE (302 L) was added into the concentrate. The mixture was agitated, then left quiescent to settle. The layers were split, and the organic layer was washed with 3 aliquots of water (42 L each aliquot).

After washing, the organic layer was concentrated at 30° C. to 55° C. under vacuum (80 mbar to 120 mbar) until distillation ceased. Methanol (130 L) was added to the concentrate. The mixture was heated to 30° C. to 50° C. under slight vacuum (80 mbar to 120 mbar) and 43 L of methanol was distilled off. The solution thus obtained was evaluated by HPLC and found to contain an amount of the compound of Formula IV equal to a 72% yield based on the amount of the compound of Formula III employed in the reaction.

Example 3: Preparation of Compound V: (2S)-2-({(1R)-1-[3,5-bis(trifluoromethyl)phenyl]ethoxy}methyl)-5-nitro-2-phenylpiperidine

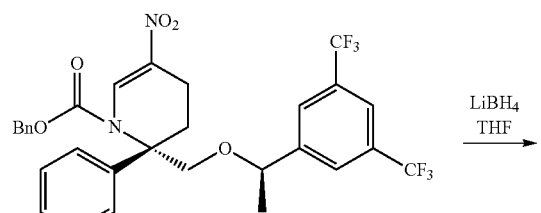

Compound IIIb

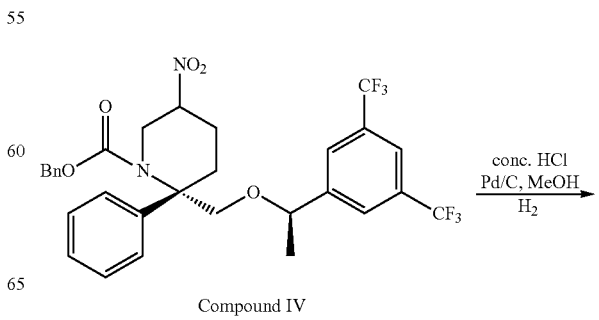

Compound IV

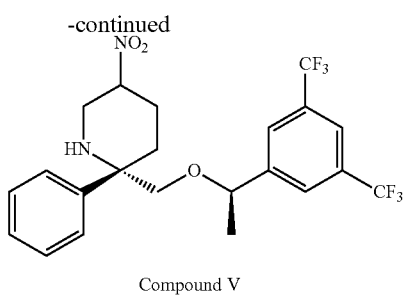

Compound V

The solution containing the compound of Formula IV prepared in the previous step (53.8 kg, 18.8 kg active, 30.7 moles of Formula IV) was diluted with methanol (90 liters). Aqueous concentrated hydrochloric acid (5.1 liters) was slowly added to the agitated solution while maintaining the mixture at a temperature of between 20° C. to 30° C. Into a separate vessel containing palladium on charcoal catalyst (1.5 kg, 10% on charcoal, 54% water) was slowly added Methanol (19 liters) while the mixture was slowly agitated to form a catalyst suspension. While continuing to slowly agitate the suspension, the solution of compound IV was slowly added to the suspension while maintaining the mixture at a temperature of from 20° C. to 25° C. After all of the solution of compound IV had been added, the mixture was placed under 1-3 bar of hydrogen pressure and agitated vigorously while maintaining the reaction mixture at a temperature of between 20° C. and 25° C. until the reaction was complete as determined by HPLC. The reaction mixture was filtered through Dicalite® (0.5 kg) and the filter cake washed with methanol, which was combined with the filtrate. The filtrate was placed under vacuum (500 mbar) and concentrated while maintaining the temperature of the filtrate between 20° C. and 30° C. until distillation ceased. During the concentrating procedure, when the mixture was concentrated to about 20% of the initial volume, the mixture was analyzed by HPLC.

After the mixture had been concentrated, toluene (113 L) was added to the concentrate. The pH of the residue was adjusted by addition of sodium carbonate solution (7.8 Kg sodium carbonate dissolved in 79 L of water) to a value between pH 9 and pH 10. When the desired pH range had been achieved, the mixture was settled and split. The organic layer was washed with a sodium chloride solution (11.3 Kg sodium carbonate dissolved in 102 L of water) and concentrated under vacuum (80 mbar to 120 mbar) while maintaining it at a temperature of 30° C. to 60° C. until distillation ceased. To the concentrate was added toluene (57 L) which was distilled off azetropically at 30° C. to 60° C. under vacuum. A second aliquot of toluene (57 L) was added and distilled off azetropically at 30° C. to 60° C. under vacuum. Karl Fischer titration indicated that the concentrate contained less than 0.2% water.

To the concentrate was added 2 aliquots of n-hexane (57 L each). Each of the hexane aliquots was subsequently distilled off under vacuum maintaining the mixture at 30° C. to 60° C. until distillation ceased. The resulting solution was evaluated by HPLC and found to contain an amount of the compound of Formula V equal to a 93% yield based on the amount of compound IV initially used. This solution was used in the subsequent step.

Example 4: Preparation of Compounds 27a and 27b

Methyl 3-[(3R/S,6S)-6-({(1R)-1-[3,5-bis(trifluoromethyl)phenyl]ethoxy}methyl)-3-nitro-6-phenylpiperidin-3-yl]propanoate

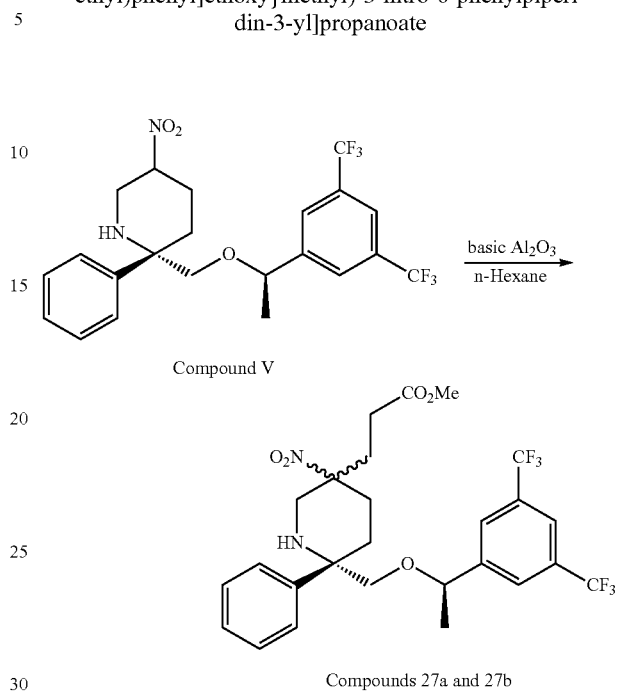

Compounds 27a and 27b

Into a vessel was placed N-hexane (106 liters). With stirring, 135.8 Kg of basic aluminum oxide was added (Brockmann IV, water content 9-14%, Camag, used as received) to form a suspension. The solution containing 29.2 kg (13.5 kg active, 28.4 moles) of the compound of Formula V prepared in the previous step was added to the suspension while stirring was continued and the mixture temperature was maintained at a temperature between 20° C. and 25° C. The equipment was rinsed with additional hexane and agitation of the reaction mixture was continued for 20 to 30 minutes after all of the solution had been added to the suspension. Into the reaction mixture was added 14.74 kg (171.2 moles) methyl acrylate maintaining the reaction mixture at a temperature between 20° C. and 25° C. The equipment was rinsed with additional n-hexane and the mixture was maintained at ambient temperature until the reaction was completed as determined by HPLC. At the end of the reaction, the reaction mixture was filtered and the filter cake was washed with toluene. The combined filtrate and wash were concentrated by applying a vacuum and maintaining the temperature of the filtrate between 30° C. and 60° C. until the filtrate is concentrated to the smallest volume that permits it to maintain a free-flowing characteristic. The concentrate was evaluated by HPLC and found to contain an amount of the compounds of Formulae 27a and 27b equivalent to a yield of 71% based on the amount of the compound of Formula V used initially. In determining yield it was found that the product contained both diastereomers in a 2:1 ratio of the compound of Formula 27a (S-diastereomer) to the compound of Formula 27b (R-diastereomer) and the yield of the desired S-diastereomer (compound 27a) was 48% based on the amount of compound V initially used, (solution yields). The solution was used directly to prepare the methylsulfonate salt in the next step.

Example 5: Preparation of sulfonate salts of Compounds of Formula 27a/27b

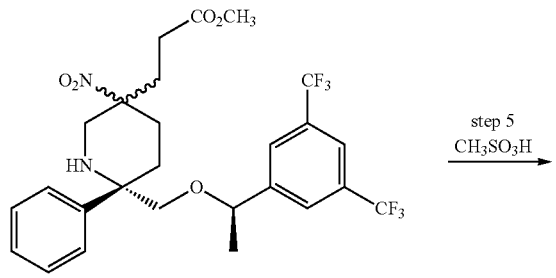

Compounds 27a and 27b step 5
CH₃SO₃H
→

Compound 27a-sulfonate (98%)

+

Compound 27b-sulfonate
(less than 2%)

To the solution containing compounds of the Formulae 27a and 27b free base prepared in Step 5 (containing 22.78 kg of both diastereomers, including 15.6 kg (27.7 moles) of the S-isomer) was added 62 liters of MTBE maintaining the temperature of the mixture at 20° C. to 25° C. The solution was passed through a fine filter and the filter was rinsed with MTBE. The clear filtrate thus obtained was concentrated to about 3× at 30° C. to 55° C. under slight vacuum (500 mbar). The concentrate was diluted with toluene and the temperature of the mixture was adjusted to 20° C. to 25° C. Methane sulfonic acid (2.0 Kg, 0.75 eq) was added to the mixture over 20 to 30 minutes while maintaining the reaction mixture at a temperature between 20° C. and 25° C. After acid addition the reaction mixture was agitated for 15 to 20 minutes. An additional 2.1 Kg (0.79 eq) of methanesulfonic acid was added to the suspension while maintaining the temperature and agitation. The reaction mixture was agitated at 20° C. to 25° C. for an additional 50 to 60 minutes following addition and then cooled to a temperature between 0° C. and 5° C., then agitated for an additional 50 to 60 minutes. At the end of the agitation period the reaction mixture was filtered, the wet cake was washed with a 1:1 mixture of MTBE/toluene at 0° C. to 5° C. The filter cake (wet) was suspended in MTBE and agitated for 50 to 60 minutes while maintaining the suspension temperature at a temperature between 20° C. and 25° C. At the end of the agitation time, the suspension was cooled and maintained at a temperature between 0° C. and 5° C. and agitated for an additional 50 to 60 minutes.

The batch was filtered and washed with 0° C. to 5° C. MTBE. The wet cake was maintained at a temperature of between 30° C. and 40° C. and dried under vacuum (150 mbar to 200 mbar), and then for an additional 4 to 5 hours at 45° C. to 50° C. under vacuum. The solids thus obtained were evaluated by HPLC and found to contain an amount of the compound of Formula 27a-sulfonate (S-isomer) equivalent to a yield of 88% based on the amount of S-isomer initially present in the mixture. HPLC analysis indicated also that the salt precipitated had an isomeric ratio of 98% S-enationmer (27a-sulfonate, desired): 2% R-enantiomer (27b-sulfonate, undesired). The solid thus obtained was used directly in the next step.

Example 8: Preparation of Formula I Compound Salt: (5S,8S)-8-({(1R)-1-[3,5-Bis(trifluoromethyl)phenyl]ethoxy}methyl)-8-phenyl-1,7-diazaspiro[4.5]decan-2-one hydrochloride monohydrate

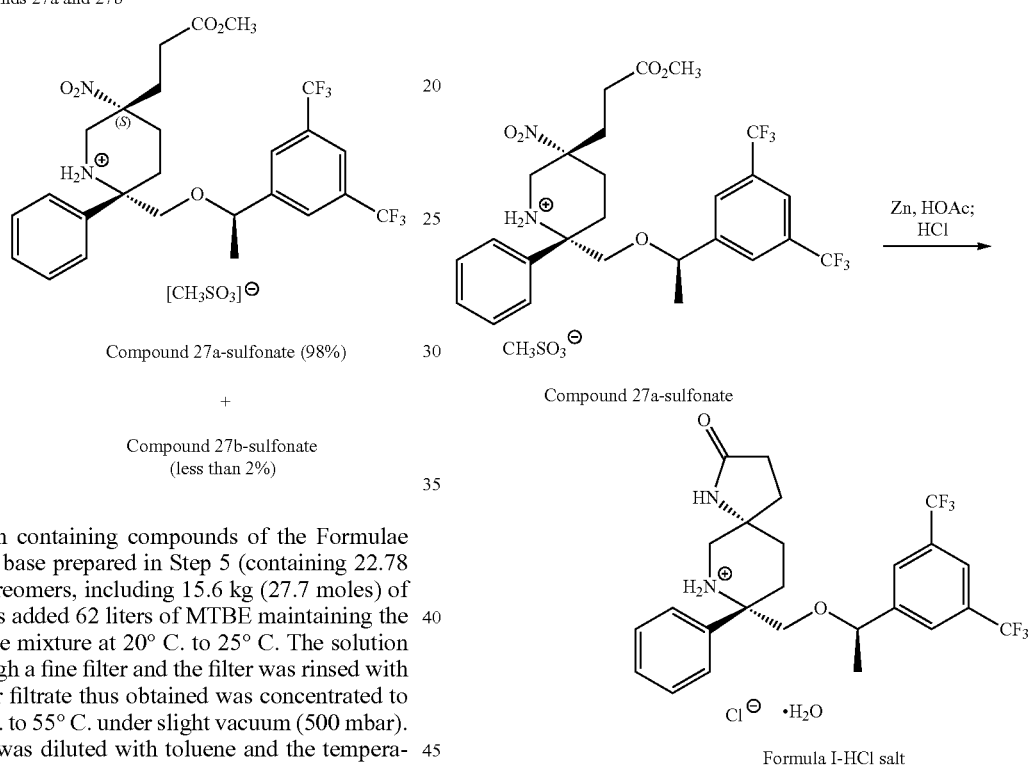

Formula I-HCl salt

Example 6A—Preparation of the compound of Formula I from 27a-sulfonate

A suspension was made by adding zinc powder (12.2 Kg, 186.6 moles) to 42 liters of concentrated acetic acid with vigorous stirring. In a separate vessel was placed 4.04 Kg of the starting material prepared in Example 5, above, and 4.1 Kg of a compound 27a-sulfonate compound prepared in a similar reaction which yielded a salt comprising 88.2% S-enantiomer and 7.8% R-enantiomer (total 8.14 kg of the sulfonate salts, about 95% S-enantiomer). The sulfonate salts were dissolved in 82 liters of concentrated acetic acid heated to 45° C. to obtain a solution. When all of the solids had dissolved the solution temperature was adjusted and maintained at a temperature between 20° C. and 30° C. The solution containing the compound of Formula 27a-sulfonate was added to the stirring zinc suspension while maintaining the mixture at a temperature below 60° C. After all of the solution was added, the reaction mixture temperature was adjusted and maintained at a temperature of from 55° C. to 60° C. until the reaction was complete, as determined by HPLC. At the end of the reaction the reaction mixture was then cooled and maintained at a temperature of from 20° C. to 30° C.

The reaction mixture was filtered through Hyflo (4.12 kg) and the wet cake was washed with toluene. The wash was combined with the filtrate and the mixture was concentrated under vacuum (80 mbar to 120 mbar) by maintaining the reaction mixture temperature between 30° C. and 60° C. until distillation ceased. To the concentrate was added 41 L of toluene. The resulting organic solution was washed successively with aliquots of 2N hydrochloric acid solution (45 L), sodium carbonate solution (2 aliquots of 82 t each, 8% solution) and sodium chloride solution (22 L, 10% solution). The washed solution was filtered and the filter rinsed with toluene which was combined with the filtrate. The filtrate was seeded with seed crystals of the compound of Formula I maintaining the filtrate at a temperature between 20° C. and 25° C. Concentrated hydrochloride acid was slowly added to the filtrate followed by fine spirit (95:5 ethanol, isopropanol) maintaining the mixture at a temperature between 20° C. and 25° C. The mixture was agitated at 20° C. to 25° C. for 25 to 35 minutes and then cooled to 0° C. to 5° C. and agitated for 25 to 35 minutes. The mixture was filtered and the wet cake washed with an aliquot of a 1:1 mixture of toluene/MTBE (10 L), followed by a second aliquot of MTBE (10 L) maintained at 20° C. to 25° C. The wet cake was dried at 40° C. to 45° C. under vacuum. The yield of crude Compound I was 88%.

The crude crystals of compound I (14.54 kg, 25.6 moles) were recrystalized by dissolving the crude compound in a mixture of fine spirit (35 liters; 95:5 ethanol/isopropanol), water with endotoxin control (35 liters) and hydrochloride acid (0.3 liter, 37%), and heating the solution to reflux with agitation. The refluxing solution was cooled and maintained at a temperature of between 74° C. to 77° C., and filtered through a preheated pipe and in-line filter. The apparatus was rinsed with a mixture of fine spirit (95:5 ethanol/isopropanol) and water with endotoxin control maintained at 60° C. to 70° C. and combined with the filtrate. The temperature of the solution thus provided was adjusted and maintained at a temperature between 72° C. and 74° C. and Compound I seed crystals were added. The seeded solution was maintained at this temperature for 15 to 20 minutes and then cooled to a temperature between 0° C. and 5° C. at the rate of 0.5° C. per minute. The seeded solution was maintained at a temperature between 0° C. and 5° C. and agitated for 30 to 40 minutes. At the end of the time the resulting mixture was filtered and washed with a 40:60 mixture of fine spirit (95:5 ethanol/isopropanol)/water with endotoxin control at 0° C. to 5° C. The wet cake was dried under vacuum (150 mbar to 200 mbar) at 35° C. to 40° C. under vacuum. The yield of the compound of Formula I was determined by HPLC to be 97% based on the amount of the S-isomer present in the solids used initially.

A second run was carried out in accordance with the foregoing, however, at the end of the reaction period the reaction mixture was extracted with aqueous sodium carbonate solution and the phases were split. The organic phase was added to dilute HCl to provide spontaneous crystallization. In a subsequent run, when spontaneous crystallization did not occur, seed crystals were charged to seed crystal formation. Once crystalline product had precipitated, the product was filtered and the cake washed successively with aliquots of water, a 1:1 mixture (vol.) of toluene:MTBE, and MTBE. The cake thus obtained was dried under vacuum at 40°-45° C. for approximately 8 h.

Example 6B—Reduction of the Compound of Formula Ia1

Preparation of the compound of Formula I with co-production of a significant amount of the compound of Formula Ia1 was carried out using the procedure described in Example 6A but starting with 47 Kg of the compound of Formula 27a-sulfonate and utilizing an industrial scale reactor. The product of the reaction was found to contain 35 mole % of the compound of Formula I and 46 mole % of the compound of Formula Ia1. At the end of the reaction the reaction mixture was was filtered through Hyflo (4.12 kg) and the wet cake was washed with toluene. The wash was combined with the filtrate and the mixture was concentrated under vacuum (80 mbar to 120 mbar) by maintaining the reaction mixture at a temperature of less than about 60° C. until a residue which was capable of being stirred was obtained. The residue was azeotropically distilled with denatured ethanol until distillation ceased then diluted with an additional aliquot of ethyl alcohol. Into a separate reactor, with stirring, was charged Raney Nickel (ca. 25 kg) and ethanol denatured with toluene. The reactor was stirred for 20 min and the liquid decanted off. The Raney Nickel was re-slurried with ethanol and the liquid decanted until the moisture content of the residue was acceptable for running a hydrogenation reaction. When the moisture content was acceptable, the reactor was charged with additional ethanol and the catalyst was transferred to an autoclave with agitation as an ethanol slurry. The product mixture prepared as described above was added to the autoclave and the batch hydrogenated at 5 bar $H_2$ pressure at ca. 50° C. until a mixture of 81.5 mole % of the compound of Formula I and 1.9 mole % of the compound of Formula Ia1 was observed in the reaction mixture. The reaction mixture thus obtained was filtered and the resulting filter cake rinsed with ethanol and combined with the filtrate. The filtrate was concentrated under vacuum to a stirrable residue, azeotropically distilled with ethanol, and when distillation ceased, the residue was diluted with an additional aliquot of ethanol. A dilute solution of aqueous HCl was added to the ethanol solution with stirring over 20 minutes and the mixture was stirred for an additional 15 minutes. The resulting reaction mixture was filtered, and the cake washed successively with aliquots of water, a 1:1 mixture of MTBE:toluene, and MTBE. The washed cake was dried under vacuum at 40°-45° C. for about 8 hours and sampled for residual solvent and water content. The hydrogenation reaction over Raney nickel yielded about 60% of the compound of Formula I based on the amount of compound of Formula V employed.

Example 7: Isomer Ratio Control by Varying Michael Addition Reaction Conditions

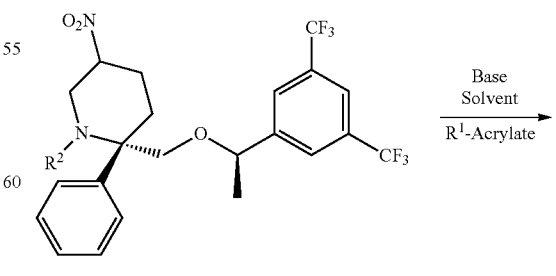

V $R^2$ = Cbz, H

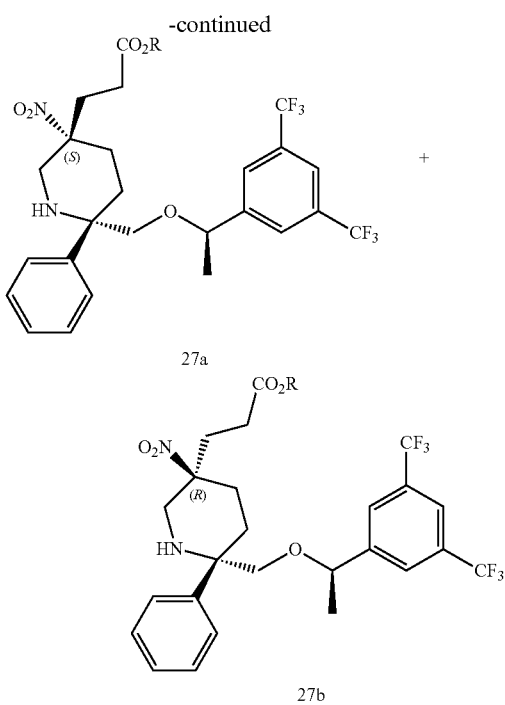

27a

27b

The Michael addition reaction shown was carried out by dissolving a weighed amount of the compound of Formula V (reactions were run using from about 200 mg to about 10 g of Formula V, depending upon the acrylate employed) into the solvent shown in the tables below. The solution was stirred at a selected temperature while adding approximately 56 equivalents of Brockmann activity IV alumina obtained from Aldrich or Camag (residual water content 7 wt. % to 12 wt. %, used as received). After 10 minutes of additional stirring, 5 equivalents of the R-acrylate indicated in the tables below was added and stirring was maintained for 20 hours. At the end of the reaction time the reaction mixture was analyzed by HPLC for the combined amount of the compounds of Formulae 27a and 27b and ratio of the compounds of Formulae 27a and 27b produced in the reaction.

TABLE 1

Effects of; (i) Varying oxide catalyst; (ii) Running Michael addition in the presence or absence of a piperidine nitrogen protecting group; and (iii) Varying the "R" group of the acrylate.

| No. | "R" group of $R^2$-acrylate | Isomer Ratio (S:R) - Base = Brockman Activity I $R^2$ = H | Isomer Ratio (S:R) - Base = MgO $R^2$ = H | Isomer Ratio (S:R) - Base = Brockman Activity I $R^2$ = Cbz | Isomer Ratio (S:R)- Base = MgO $R^2$ = Cbz |
|---|---|---|---|---|---|
| 1 | Methyl | 63/37 | | | 20/80 |
| 2 | (−)-8-Phenylmethyl | 78/22 | | 25/75 | 15/85 |
| 3 | Phenyl | 66/34 | | | |
| 4 | t-Butyl | 69/31 | 34/66 | 30/70 | 25/75 |
| 5 | Isobornyl | 84/16 | | 23/77 | 18/82 |
| 6 | 1-adamantanyl | 69/31 | | | |
| 7 | 2-adamantanyl | 85/15 | | | |
| 8 | adamantane methanyl | 86/14 | | | |
| 9 | cis-Pinan-2-yl | 66/34 | | | |
| 10 | (+)-Isopinocampheyl | 73/27 | | | |

The reactions run for Table I were carried out using a weight of n-hexane 14× the weight of the acrylate employed in the reaction. Reactions were run at ambient temperature (about 20° C. to 25° C.). The data shown in Table 1 indicates that, for some acrylate acceptors, the presence of a protecting group on the piperidine nitrogen can reverse the selectivity of the Michael addition reaction for the preferred isomer. It indicates also that basic alumina is the preferred base catalyst for promoting formation of the preferred isomer, and that selecting a sterically demanding acrylate, for example adamantane methanyl-acrylate, promotes preferentially the formation of the desired isomer.

TABLE II

Effect of Solvent on Isomer Produced in the Michael Addition Step

| Run No. | Solvent | Isomer Ratio Produced (S-isomer:R-isomer) |
|---|---|---|
| 1 | n-Hexane | 79:21 |
| 2 | Toluene | 84:16 |
| 3 | Methanol | 48:52 |
| 4 | Dimethylformamide | 38:62 |
| 5 | Tetrahydrofuran | 51:49 |

The data in Table II were generated using the above-described addition reaction employing Brockman activity IV basic alumina and (−)-8-phenylmenthyl acrylate as the Michael acceptor with the deprotected substrate compound of Formula V (thus "$R^2$"=H). All runs were conducted at ambient temperature (about 20° C. to 25° C.). These results indicate that non-polar solvents, for example n-hexane, or low polarity non-protic solvents, for example toluene, promote formation of the desired isomer.

TABLE III

Influence of Alumina Activity Stage on Selection of Preferred Isomer

| Run No. | Base | Isomer Ratio (S-isomer:R-isomer |
|---|---|---|
| 1 | Neutral Alumina Brockman Activity I | 63:37 |
| 2 | Basic Alumina Brockman Activity I | 51:49 |
| 3 | Basic Alumina Brockman Activity II | |
| 4 | Basic Alumina Brockman Activity III | |
| 5 | Basic Alumina Brockman Activity IV | 70:30 |

These reactions were run using methyl acrylate as the Michael acceptor, with a deprotected substrate (therefore "R*"=H) in n-hexane at 20° C. to 25° C. The data in Table III indicates that the best selectivity for the desired S-isomer is observed utilizing basic alumina having a Brockman activity level of IV. It was also found that conversion yields on Brockman activity I material were very low, typically 37% conversion after reactions times comparable to those yielding complete conversion with Brockman activity level IV alumina.

The above description of the invention is intended to be illustrative and not limiting. Various changes or modifications in the embodiments described herein may occur to those skilled in the art. These changes can be made without departing from the scope or spirit of the invention

What is claimed is:

1. A compound of the formula:

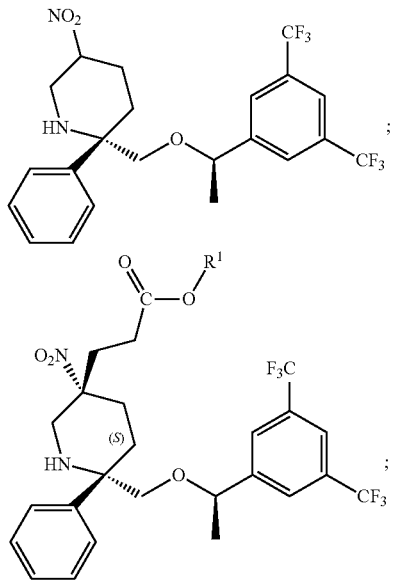

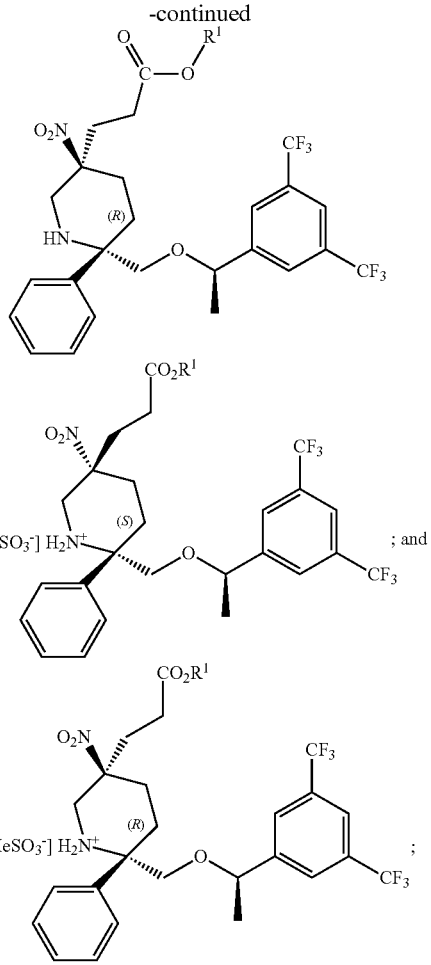

wherein
R[1] is cyclic alkyl having up to 6 carbon atoms, phenyl, 2-methoxy-ethyl, 2 (dimethylamino)ethyl, (L)-menthyl, (D)-menthyl, dimethylamide, (R) benzyl-oxazolidinonamide, (S)-benzyl-oxazolidinonamide, isobornyl, cis-pinan-2-yl, isopinocampheyl, adamantylmethyl, 2-adamantyl, 1-adamantyl, or (−)-8 phenylmenthyl.

* * * * *